(12) United States Patent
Malin et al.

(10) Patent No.: US 6,280,381 B1
(45) Date of Patent: Aug. 28, 2001

(54) INTELLIGENT SYSTEM FOR NONINVASIVE BLOOD ANALYTE PREDICTION

(75) Inventors: Stephen F. Malin, Phoenix; Timothy L. Ruchti, Gilbert, both of AZ (US)

(73) Assignee: Instrumentation Metrics, Inc., Chandler, AZ (US)

( * ) Notice: Subject to any disclaimer, the term of this patent is extended or adjusted under 35 U.S.C. 154(b) by 0 days.

(21) Appl. No.: 09/359,191

(22) Filed: Jul. 22, 1999

(51) Int. Cl.$^7$ ....................................................... A61B 5/00
(52) U.S. Cl. ............................................. 600/322; 128/920
(58) Field of Search ...................................... 600/310, 322, 600/323, 330, 331, 336, 473; 128/920, 924, 925; 356/402; 250/340, 341.1, 339.01

(56) References Cited

U.S. PATENT DOCUMENTS

| | | | |
|---|---|---|---|
| 5,424,545 | * 6/1995 | Block et al. | 250/341.1 |
| 5,435,309 | 7/1995 | Thomas et al. | |
| 5,553,616 | * 9/1996 | Ham et al. | 128/925 |
| 5,576,544 | 11/1996 | Rosenthal | 250/341.1 |
| 5,606,164 | 2/1997 | Price et al. | 250/339.09 |
| 5,725,480 | 3/1998 | Oosta et al. | 600/310 |
| 5,798,526 | 8/1998 | Shenk et al. | 250/339.09 |

FOREIGN PATENT DOCUMENTS

| | | |
|---|---|---|
| WO 92/22804 | 12/1992 | (WO) . |
| WO 95/13739 | 5/1995 | (WO) . |
| WO 97/28437 | 8/1997 | (WO) . |

OTHER PUBLICATIONS

Roe et al., Bloodless Glucose Measurements, Critical Reviews in Therapeutic Drig Carrier Systems, 1998.
Khalil, Spectroscopic and Clinical Aspects of Noninvasive Glucose Measurements, 1999, Clinical Chemistry.
Cheong et al., A Review of the Optical Properties of Biological Tissues, 1990, IEEE.
Benaron et al., Imaging and Quantitations in Tissue Using Time–Resolved Spectrophotometry: The Impact of Statically and Dynamically Variable Optical Path Lengths.
Conway et al., A New Approach for the Estimation of Body Composition: Infrared Interactance, Dec. 1984, The Journal of Clinical Nutrition.
Homma et al, Influence of Adipose Tissue Thickness on Near Infrared Spectrscopic Signals in the Measurement of Human Muscle, Oct. 1996, Journal of Biomedical Optics.
Profio, Light transport in tissue, Jun. 15, 1989, Applied Optics.

(List continued on next page.)

*Primary Examiner*—Eric F. Winakur
(74) *Attorney, Agent, or Firm*—Michael A. Glenn; Christopher Peil

(57) ABSTRACT

An intelligent system for measuring blood analytes noninvasively operates on a near infrared absorbance spectrum of in vivo skin tissue. An hierarchical architecture employs a pattern classification engine to adapt the calibration to the structural properties and physiological state of the subject as manifested in the absorbance spectrum. A priori information about the primary sources of sample variability are used to establish general categories of subjects. By applying calibration schemes specific to the various categories, the spectral interference is reduced resulting in improved prediction accuracy and parsimonious calibrations. Two classification rules are disclosed. The first rule assumes the classes are mutually exclusive and applies specific calibration models to the various subject categories. The second rule uses fuzzy set theory to develop calibration models and blood analyte predictions. Therefore, each calibration sample has the opportunity to influence more than one calibration model according to its class membership. Similarly, the predictions from more than one calibration are combined through defuzzification to produce the final blood analyte prediction.

51 Claims, 17 Drawing Sheets

OTHER PUBLICATIONS

Gemert et al., Skin Optics, Dec. 1989, IEEE Transactions on Biomedical Engineering.

Wilson et al., Optical reflectance and transmittance of tissues: Principles and Applications, Dec. 1990, IEEE Journal of Quantum Electronics.

Robinson et al, Noninvasive Glucose Monitoring in Diabetic Patients: A Preliminary Evaluation, 1992, Clin. Chem.

Antsaklis, Introduction to Intelligent Control Systems with High Degrees of Autonomy, Introduction to Intelligent Control Systems.

Duda, *Pattern Classification and Scene Analysis*, 1973 John Wiley & Sons Publication.

Hazen, *Glucose Determination in Biological Matrices Using Near–Infrared Spectroscopy*, Aug. 1995, University of Iowa.

Schurmann, *Pattern Classification—A unified View of Statistical and Neural Approaches*, John Wiley & Sons Publication.

Martin, Direct Measurment of Moisture in Skin by NIR Spectroscopy, Sep./Oct. 1993, J. Soc. Cosmet. Chem.

Andrew et al, Changes with Advancing Age in the Cell Population of Human Dermis, 1964/65, Gerontologia.

Montagna, Structural Changes in Aging Human Skin, 1979, The Journal of Investigative Dermatology.

Bocklehurst, *Textbook of Geriatric Medicine and Gerontology*, 1973, University of Manchester, London.

*Fuzzy Models for Pattern Recognition—Methods that Search for Structures in Data*, IEEE Press.

Kowalski, Chemometrics: Theory and Application, 1976, ACS Symposium Series.

Haykin, *Neural Networks—A comprehensive Foundation*, 1994, Prentice–Hall.

Zadeh, Fuzzy Sets, 1965, Inform.Control.

Pao, *Adaptive Pattern Recognition and Neural Networks*, 1989 Addison–Wesley Publishing.

Martens, *Multivariate Calibration*, John Wiley & Sons.

Savitzky et al., Smoothing and Differentiation of Data by Simplified Least Squares Procedures, Principle Component Regression.

Geladi et al., Linearization and Scatter–Correction for Near Infrared Reflectance Spectra of Meat, 1985 Applied Spectroscopy.

Geladi et al., *Partial Least—Squares Regression: A Tutorial*, 1985, Elsevier Science Publishers.

Matcher et al., Use of the water absorption spectrum to quantify tissue chromophore concentration changes in near–infrared spectroscopy, 1993, Phys. Med. Biol.

Burmeister, In Vitro Model for Human Noninvasive Blood Glucose, 1997, These: University of Iowa.

Draper, Applied Regression Analysis, The Matrix Approach to Linear Regression, John Wiley & Sons.

Patterson, Modelling the Thermal Effects of Blood Flow in Human Skin, May 1978, The South African Mechanical Engineer.

Anderson et al., The Optics of Human Skin, 1981, Journal of Investigative Dermatology.

Schlager et al., *TAMM—a reflective, noninvasive, near infrared blood chemistry Analyzer*, Biotronics Technologies, Inc., 1995.

\* cited by examiner

Membership Rules 104

1. if Male AND Young then PLS1
2. if Male AND Old then PLS2
3. if Female AND Young then PLS3
4. if Female AND Old then PLS4

*FIG. 13*

Fuzzy Membership Rules 1. if Male AND Young then WPCR1
2. if Male AND Middle Aged then WPCR2
3. if Male AND Old then WPCR3
4. if Female AND Young then WPC4
5. if Female AND Middle Aged then WPCR5
6. if Female AND Old then WPCR6

INTELLIGENT SYSTEM FOR NONINVASIVE BLOOD ANALYTE PREDICTION

BACKGROUND OF THE INVENTION

1. Technical Field

The invention relates to the measurement of blood analytes. More particularly, the invention relates to an intelligent system for noninvasive blood analyte prediction.

2. Description of the Prior Art

The goal of noninvasive blood analyte measurement is to determine the concentration of targeted blood analytes without penetrating the skin. Near infrared (NIR) spectroscopy is a promising noninvasive technology which bases measurements on the absorbance of low energy NIR light that is transmitted into a subject. The light is focused onto a small area of the skin and propagates through subcutaneous tissue. The reflected or transmitted light that escapes and is detected by a spectrometer provides information about the tissue contents that it has penetrated.

The absorbance of light at each wavelength is a function of the structural properties and chemical composition of the tissue. Tissue layers, each containing a unique heterogeneous particulate distribution, affect light absorbance through scattering. Chemical components, such as water, protein, fat and blood analytes, absorb light proportionally to their concentration through unique absorption profiles or signatures. The measurement of blood analyte concentrations is based on detecting the magnitude of light attenuation caused by the absorption signature of the targeted analyte. The process of calibration is the development of a mathematical transformation or model which estimates the blood analyte concentration from the measured tissue absorbance spectrum.

However, accurate noninvasive estimation of blood analytes is presently limited by the dynamic nature of the sample, the skin and living tissue of the subject. Chemical, structural and physiological variations occur that produce dramatic changes in the optical properties of the tissue sample.

See, for example, R. Anderson, J. Parrish, *The optics of human skin*, Journal of Investigative Dermatology, vol. 77(1), pp. 13–19 (1981); W. Cheong, S Prahl, A. Welch, *A review of the optical properties of biological tissues*, IEEE Journal of Quantum Electronics, vol. 26(12), pp. 2166–2185 (December 1990); D. Benaron, D. Ho, *Imaging (NIRI) and quantitation (NIRS) in tissue using time-resolved spectrophotometry: the impact of statically and dynamically variable optical path lengths*, SPIE, vol. 1888, pp.10–21 (1993); J. Conway, K. Norris, C. Bodwell, *A new approach for the estimation of body composition: infrared interactance*, The American Journal of Clinical Nutrition, 40, pp. 1123–1140 (December 1984); S. Homma, T. Fukunaga, A. Kagaya, *Influence of adipose tissue thickness in near infrared spectroscopic signals in the measurement of human muscle*, Journal of Biomedical Optics, 1(4), pp. 418–424 (October 1996); A. Profio, *Light transport in tissue*, Applied Optics, vol. 28(12), pp. 2216–2222 (June 1989); and M. Van Gemert, S. Jacques, H. Sterenborg, W. Star, *Skin optics*, IEEE Transactions on Biomedical Engineering, vol. 36(12), pp. 1146–1154 (December 1989).

These variations include the following general categories:

1. Covariation of spectrally interfering species. The NIR spectral absorption profiles of blood analytes tend to overlap and vary simultaneously over brief time periods. This produces spectral interference and necessitates the measurement of absorbance at more independently varying wavelengths than the number of interfering species.

2. Sample heterogeneity. The tissue measurement site has multiple layers and compartments of varied composition and scattering. The spectral absorbance versus wavelength is related to a complex combination of the optical properties and composition of these tissue components. Therefore, a general representation or model of the tissue absorbance spectrum is nonlinear and difficult to realize on the basis of first principles.

3. State Variations. Variations in the subject's physiological state effect the optical properties of tissue layers and compartments over a relatively short period of time. Such variations, for example, may be related to hydration levels, changes in the volume fraction of blood in the tissue, hormonal stimulation, temperature fluctuations and blood hemoglobin levels.

4. Structural Variations. The tissue characteristics of individuals differ as a result of factors that include hereditary, environmental influences, the aging process, sex and body composition. These differences are largely anatomical and can be categorized as slowly varying structural properties producing diverse tissue geometry. Consequently, the tissue of a given subject has distinct systematic spectral absorbance features or patterns that can be related directly to specific characteristics such as dermal thickness, protein levels and percent body fat. While the absorbance features are repeatable by subject, over a population of subjects they produce confounding nonlinear spectral variation. Therefore, differences between subjects are a significant obstacle to the noninvasive measurement of blood analytes through NIR spectral absorbance. In a non-dispersive system, variations similar to (1) above are easily modeled through multivariate techniques, such as multiple linear regression and factor based algorithms. Significant effort has been expended to model the scattering properties of tissue in diffuse reflectance although the problem outlined in (2) above has been largely unexplored. Variations of the type listed in (3) and (4) above causes significant nonlinear spectral variation for which an effective solution has not been reported. For example, several reported methods of noninvasive glucose measurement develop calibration models that are specific to an individual over a short period of time.

See, for example, K. Hazen, *Glucose determination in biological matrices using near-infrared spectroscopy*, Doctoral Dissertation, University of Iowa (August 1995); J. Burmeister, *In vitro model for human noninvasive blood glucose measurements*, Doctoral Dissertation, University of Iowa (December 1997); and M. Robinson, R. Eaton, D. Haaland, G. Koepp, E. Thomas, B. Stallard, P. Robinson, *Noninvasive glucose monitoring in diabetic subjects: a preliminary evaluation*, Clin. Chem, 38/9, pp. 1618–1622 (1992).

This approach avoids modeling the differences between subjects and therefore cannot be generalized to more individuals. However, the calibration models have not been tested over long time periods during which variation of type (4) above may require recalibration. Furthermore, the reported methods have not been shown to be effective over a range of type (3) above variations.

It would be desirable to provide a method and apparatus for compensating for the variations described above.

SUMMARY OF THE INVENTION

The invention provides a method and apparatus for compensating for covariation of spectrally interfering species, sample heterogeneity, state variations, and structural variations through an intelligent pattern recognition system that is capable of determining calibration models that are most appropriate for the subject at the time of measurement. The calibration models are developed from the spectral absorbance of a representative population of subjects that have been segregated into groups. The groups or classes are defined on the basis of structural and state similarity, such that the variation within a class is small compared to the variation between classes. Classification occurs through extracted features of the tissue absorbance spectrum related to the current subject state and structure.

The invention provides an intelligent system for measuring blood analytes noninvasively. The system operates on a near infrared absorbance spectrum of in vivo skin tissue. The hierarchical architecture employs a pattern classification engine to adapt the calibration to the structural properties and physiological state of the subject as manifested in the absorbance spectrum. A priori information about the primary sources of sample variability is used to establish general categories of subjects. The spectral interference is reduced by applying calibration schemes specific to the various categories, resulting in improved prediction accuracy and parsimonious calibrations.

Two classification rules are disclosed:

The first rule assumes that the classes are mutually exclusive and applies specific calibration models to the various subject categories.

The second rule uses fuzzy set theory to develop calibration models and blood analyte predictions. Therefore, each calibration sample has the opportunity to influence more than one calibration model according to its class membership. Similarly, the predictions from more than one calibration are combined through defuzzification to produce the final blood analyte prediction.

BRIEF DESCRIPTION OF THE DRAWINGS

FIG. 4A shows subject classes that are mutually exclusive, and where FIG. 4B shows fuzzy classification applied to assign class membership to more than one class, both according to the invention;

FIG. 13 is a block schematic diagram showing membership rules according to the invention;

FIG. 17 is a block schematic diagram showing fuzzy membership rules according to the invention.

DETAILED DESCRIPTION OF THE INVENTION

The intelligent measurement system herein disclosed provides improved NIR noninvasive blood analyte measurement accuracy. This is accomplished by defining subpopulations or classes of subjects whose structure and state produce similarly featured NIR absorbance spectra. The classes have improved homogeneity leading to a reduction in variation related to the optical properties and composition of the sample. Because the interference is reduced while the magnitude of the blood analyte absorbance signal is unchanged, a substantial increase in signal-to-noise ratio is realized.

One goal of the intelligent measurement system (IMS) is to measure blood analytes noninvasively over a diverse population of subjects at various physiological states. The method is to classify subjects according to their state and structure and apply a combination of one or more existing calibration models to predict the blood analytes.

Figure 1:
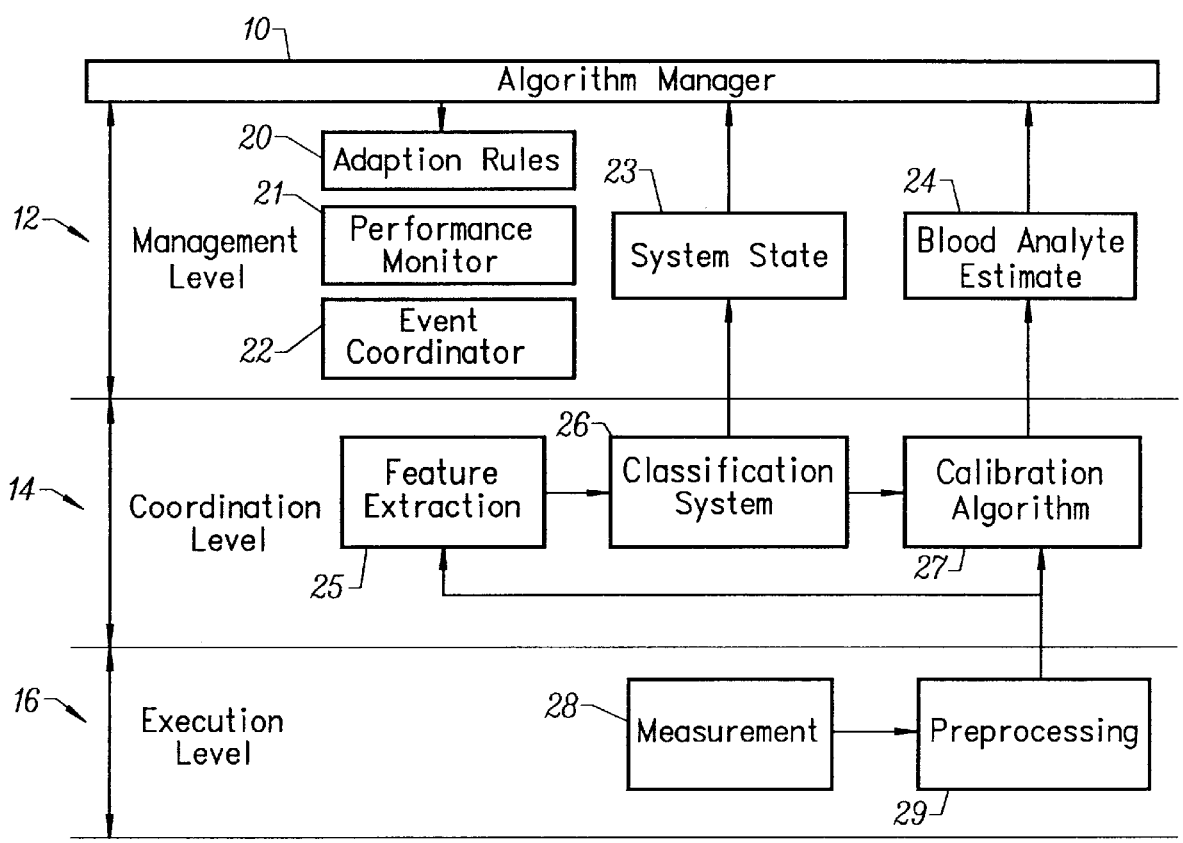
FIG. 1 is a block schematic diagram of an architecture of an intelligent system for noninvasive measurement of blood analytes according to the invention.

The architecture of the IMS is shown in FIG. 1 and consists of a conventional three-layer hierarchy (see, for example, P. Antsaklis, K.Passino, ed., *An Introduction to Intelligent and Autonomous Control,* Boston: Kluwer Academic Publishers (1992)) that operates in conjunction with an algorithm manager 10. The execution layer 16 receives the tissue absorbance spectrum from an instrument 28 and performs rudimentary preprocessing 29. The coordination layer 14 performs feature extraction 25. A classification system 26 is used to classify the subject according to extracted features that represent the state and structure of a sample. Based on the classification, the predictions from one or more existing calibration models 27 are used to form a glucose estimate 24. The classification and blood analyte prediction are passed to the management level 12 and action is taken based on the certainty of the estimate. The management level is also responsible for coordinating 22 all algorithmic events, monitoring the performance 21 based on the class, adapting the rules 20 as necessary, and maintaining information regarding system state 23.

Within the framework of FIG. 1, two different approaches to classification are proposed. The first approach uses classes that are mutually exclusive. The second approach applies fuzzy set theory to form a classifier and prediction rules which allow membership in more than one class. The framework also allows for the detection of outliers, the determination of samples that are significantly different from the existing classes, and long-term monitoring of the system performance.

Measurement and Preprocessing

Figure 2:
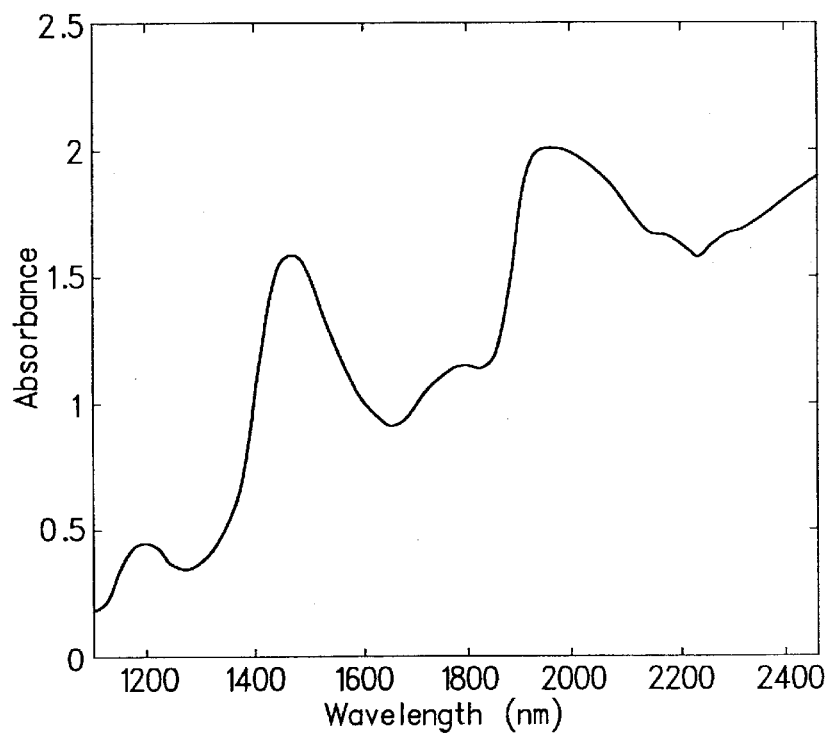
FIG. 2 is a typical noninvasive absorbance spectrum.

The sample measurement or tissue absorbance spectrum is the vector $m \in \Re^N$ of absorbance values pertaining to a set of N wavelengths $\lambda \in \Re^N$ that span the near infrared (700 to 2500 nm). A typical plot of m versus $\lambda$ is shown in FIG. 2. Assuming that variation in the target analyte is evident in a consistent absorbance signature, the absorbance measurement can be performed either transmissively, through diffuse reflectance, or through alternate methods without negatively impacting the proposed algorithm. The number of necessary wavelengths is a function of the cross correlation between the target analyte and the interfering species. For noninvasive applications with significant variation within and between individuals, the entire spectrum is useful.

Preprocessing 29 (FIG. 1) includes operations such as scaling, normalization, smoothing, derivatives, filtering and other transformations that attenuate the noise and instrumental variation without affecting the signal of interest. The preprocessed measurement, $X \in \Re^N$, is determined according to:

$$x = h(\lambda, m) \quad (1)$$

where $h: \Re^{N \times 2} \to \Re^N$ is the preprocessing function.

Pattern Recognition System

A set of subject groups or classes exists with members that are defined by the similarity of specific features. Grouping of the subjects according to the features reduces the spectral variation related the diverse structural properties of the subject population and physiological states encountered. The spectral absorbance measurements corresponding to the classes are more homogeneous than the entire population. The magnitude of the spectral signal of the target analyte, however, remains unchanged. Therefore, calibration models for predicting blood analytes that are specific to subject classes are expected to be less complex and have an improved level of accuracy.

The pattern recognition system is designed to classify new spectral measurements into the previously defined classes through structural and state similarities as observed in the tissue absorbance spectrum. Class membership is an indication of which calibration model(s) is(are) most likely to estimate the concentration of the target blood analyte accurately. Therefore, the pattern classification system is the essence of the proposed intelligent measurement system shown in FIG. 1.

Figure 3:
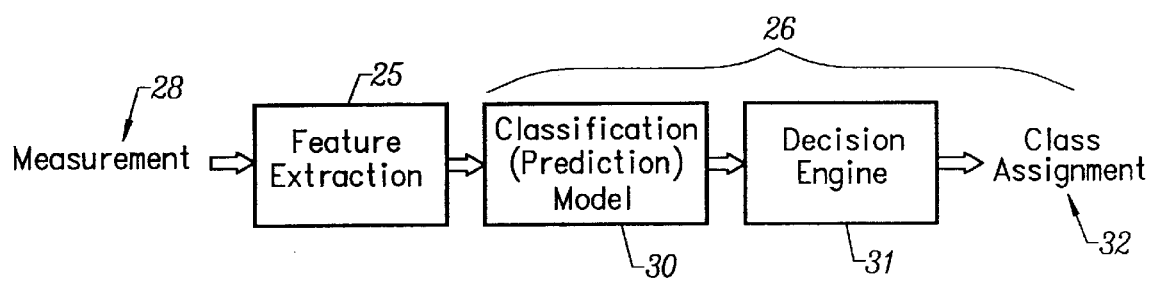
FIG. 3 is a block schematic diagram of a pattern classification system according to the invention.

FIG. 3 is a more detailed representation of the pattern classification system. The system has two general functions:

The extraction of features, and

The classification of the features according to a classification model and decision rule.

Feature extraction 25 is any mathematical transformation that enhances a particular aspect or quality of the data that is useful for interpretation. The classification model 30 is a method for determining a set of similarity measures with the predefined classes. The decision rule is the assignment of class membership 32 on the basis of a set of measures calculated by a decision engine 31 (see, for example, R. Duda, P. Hart, *Pattern Classification and Scene Analysis,* John Wiley and Sons, New York (1973); and J. Schurmann, *Pattern Classification. A Unified View of Statistical and Neural Approaches,* John Wiley & Sons, Inc., New York (1996)).

Figure 4A:
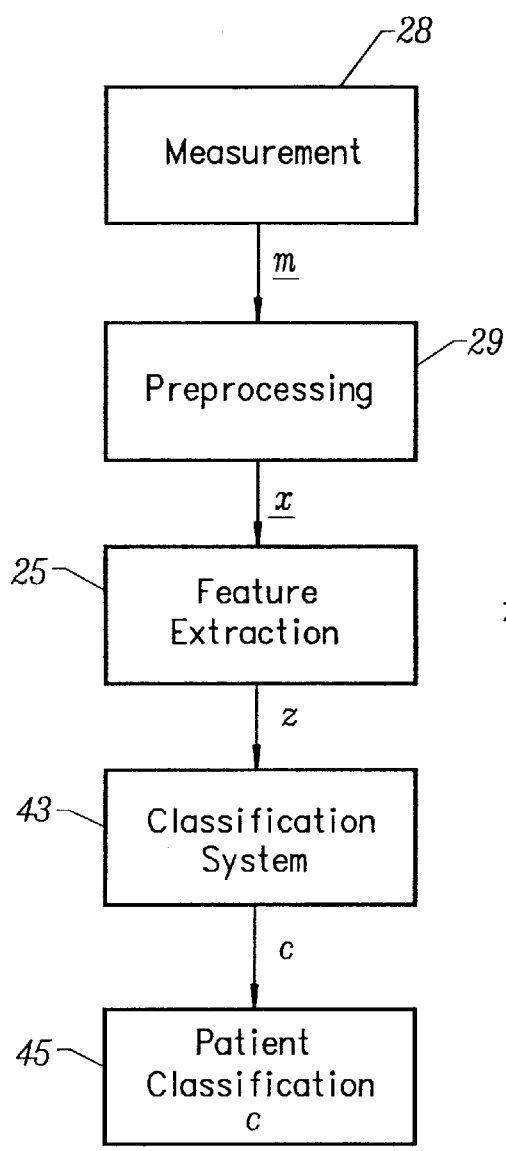
FIGS. 4A and 4B provide two different flow diagrams showing two embodiments of the herein disclosed pattern classification system, where
Figure 4B:
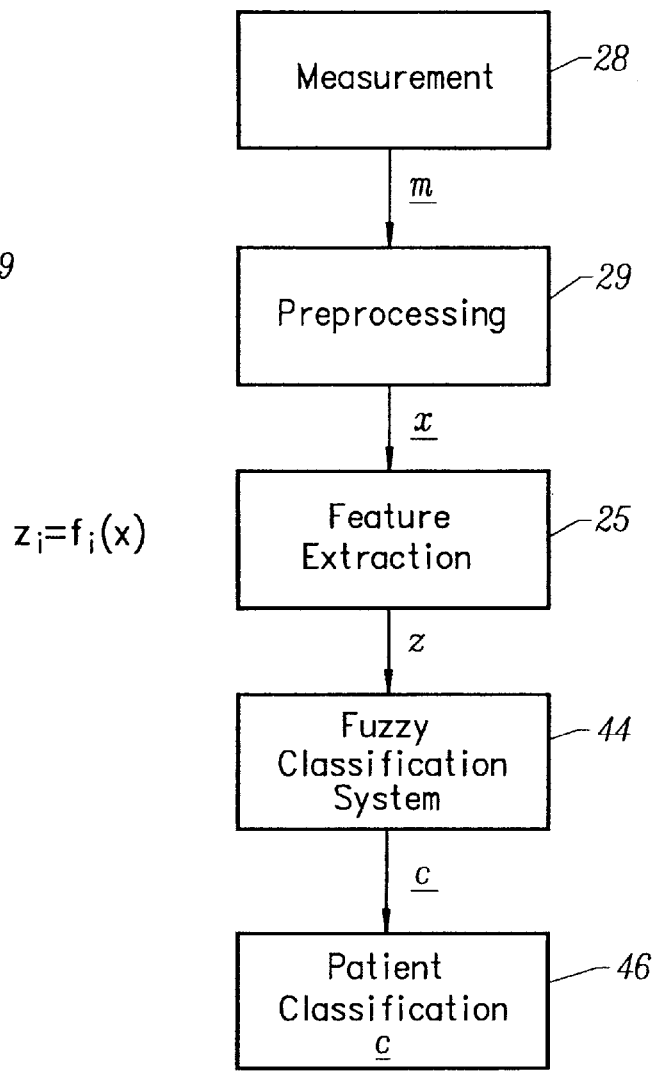

Within this framework, two different classification schemes are proposed. The first scheme, shown in FIG. 4A, provides a classification system 43 that assumes that the classes are mutually exclusive and forces each measurement to be assigned to a single class 45. The scheme shown in FIG. 4B employs a fuzzy classifier 44 that is not mutually exclusive. This allows a sample to have membership in more than one class simultaneously and provides a number between zero and one indicating the degree of membership in each class 46.

Feature Extraction

Feature extraction is any mathematical transformation that enhances a quality or aspect of the sample measurement for interpretation (see, for example, R. Duda, P. Hart, *Pattern Classification and Scene Analysis,* John Wiley and Sons, New York (1973)). The purpose of feature extraction in FIG. 1 is to represent concisely the structural properties and physiological state of the tissue measurement site. The set of features is used to classify the subject and determine the calibration model(s) most useful for blood analyte prediction.

The features are represented in a vector, $z \in \Re^M$ that is determined from the preprocessed measurement through:

$$z = f(\lambda, x) \quad (2)$$

where $f: \Re^N \to \Re^M$ is a mapping from the measurement space to the feature space. Decomposing $f(\bullet)$ yields specific transformations, $f_i(\bullet): \Re^N \to \Re^{M_i}$ for determining a specific feature. The dimension, $M_i$, indicates whether the ith feature is a scalar or a vector and the aggregation of all features is the vector z. When a feature is represented as a vector or a pattern, it exhibits a certain structure indicative of an underlying physical phenomenon.

The individual features are divided into two categories:

Abstract, and

Simple.

Abstract features do not necessarily have a specific interpretation related to the physical system. Specifically, the scores of a principal component analysis are useful features, although their physical interpretation is not always known. The utility of the principal component analysis is related to the nature of the tissue absorbance spectrum. The most significant variation in the tissue spectral absorbance is not caused by a blood analyte but is related to the state, structure, and composition of the measurement site. This variation is modeled by the primary principal components. Therefore, the leading principal components tend to represent variation related to the structural properties and physiological state of the tissue measurement site.

Simple features are derived from an a priori understanding of the sample and can be related directly to a physical phenomenon. Useful features that can be calculated from NIR spectral absorbance measurements include but are not limited to:

1. Thickness of adipose tissue (see, for example, J. Conway, K. Norris, C. Bodwell, *A new approach for the estimation of body composition: infrared interactance,* The American Journal of Clinical Nutrition, 40, pp. 1123–1140 (December 1984); and S. Homma, T. Fukunaga, A. Kagaya, *Influence of adipose tissue thickness in near infrared spectroscopic signals in the measurement of human muscle,* Journal of Biomedical Optics, 1(4), pp. 418–424 (October 1996)).

2. Tissue hydration (see, for example, K. Martin, *Direct measurement of moisture in skin by NIR spectroscopy,* J. Soc. Cosmet. Chem., vol. 44, pp. 249–261 (September/October 1993)).

3. Magnitude of protein absorbance (see, for example, J. Conway, K. Norris, C. Bodwell, *A new approach for the estimation of body composition: infrared interactance,* The American Journal of Clinical Nutrition, 40, pp. 1123–1140 (December 1984)).
4. Scattering properties of the tissue (see, for example, A. Profio, *Light transport in tissue,* Applied Optics, vol. 28(12), pp. 2216–2222 (June 1989); W. Cheong, S. Prahl, A. Welch, *A review of the optical properties of biological tissues,* IEEE Journal of Quantum Electronics, vol. 26(12), pp. 2166–2185 (December 1990); and R. Anderson, J. Parrish, *The optics of human skin,* Journal of Investigative Dermatology, vol. 77(1), pp. 13–19 (1981)).
5. Skin thickness (see, for example, R. Anderson, J. Parrish, *The optics of human skin,* Journal of Investigative Dermatology, vol. 77(1), pp. 13–19 (1981); and M. Van Gemert, S. Jacques, H. Sterenborg, W. Star, *Skin optics,* IEEE Transactions on Biomedical Engineering, vol. 36(12), pp. 1146–1154 (December 1989).
6. Temperature related effects (see, for example, A. Patterson, *Modeling the thermal effects of blood flow in human skin,* The South African Mechanical Engineer, vol. 28, pp. 179–182 (May 1978)).
7. Age related effects (see, for example, W. Andrew, R. Behnke, T. Sato, *Changes with advancing age in the cell population of human dermis,* Gerontologia, vol. 10, pp. 1–19 (1964/65); W. Montagna, K. Carlisle, *Structural changes in aging human skin,* The Journal of Investigative Dermatology, vol. 73, pp. 47–53 (1979); and J. Brocklehurst, *Textbook of Geriatric Medicine and Gerontology,* Churchill Livingstone, Edinburgh and London, pp.593–623 (1973)).
8. Spectral characteristics related to sex.
9. Pathlength estimates (see, for example, R. Anderson, J. Parrish, *The optics of human skin,* Journal of Investigative Dermatology, vol. 77(1), pp. 13–19 (1981); and S. Matcher, M. Cope, D. Delpy, *Use of water absorption spectrum to quantify tissue chromophore concentration changes in near-infrared spectroscopy,* Phys. Med. Biol., vol. 38, 177–196 (1993)).
10. Volume fraction of blood in tissue (see, for example, M. Van Gemert, S. Jacques, H. Sterenborg, W. Star, *Skin optics,* IEEE Transactions on Biomedical Engineering, vol. 36(12), pp. 1146–1154 (December 1989)).
11. Spectral characteristics related to environmental influences.
12. Hematocrit levels.

Spectral decomposition is employed to determine the features related to a known spectral absorbance pattern. Protein and fat, for example, have known absorbance signatures that can be used to determine their contribution to the tissue spectral absorbance. The measured contribution is used as a feature and represents the underlying variable through a single value.

Features related to demographic information, such as age, are combinations of many different effects that cannot be represented by a single absorbance profile. Furthermore, the relationship of demographic variables and the tissue spectral absorbance is not deterministic. For example, dermal thickness and many other tissue properties are statistically related to age but also vary substantially as a result of hereditary and environmental influences. Therefore, factor based methods are employed to build models capable of representing variation in the measured absorbance related to the demographic variable. The projection of a measured absorbance spectrum onto the model constitutes a feature that represents the spectral variation related to the demographic variable.

The compilation of the abstract and simple features constitutes the M-dimensional feature space. Due to redundancy of information across the set of features, optimum feature selection and/or data compression is applied to enhance the robustness of the classifier.

Classification

Feature extraction determines the salient characteristics of measurements that are relevant for classification. The goal of the classification step is to determine the calibration model (s) that is/are most appropriate for the measurement. In this step, the subject is assigned to one of many predefined classes for which a calibration model has been developed and tested. Because the applied calibration model is developed for similar tissue absorbance spectra, the blood analyte predictions are more accurate than those obtained from a universal calibration model.

As depicted in FIG. 3, pattern classification generally involves two steps:

A mapping (30), and

A decision engine (31).

The mapping measures the similarity of the features to predefined classes and the decision engine assigns class membership.

In the following discussion, two general methods of classification are described. The first method uses mutually exclusive classes and therefore assigns each measurement to one class. The second method uses a fuzzy classification system that allows class membership in more than one class simultaneously. Both methods require prior class definitions as described subsequently.

Class Definition

The development of the classification system requires a data set of exemplar spectral measurements from a representative sampling of the population. Class definition is the assignment of the measurements in the exploratory data set to classes. After class definition, the measurements and class assignments are used to determine the mapping from the features to class assignments.

Class definition is performed through either a supervised or an unsupervised approach (see, for example, J. Schurmann, *Pattern Classification. A Unified View of Statistical and Neural Approaches,* John Wiley & Sons, Inc., New York (1996)). In the supervised case, classes are defined through known differences in the data. The use of a priori information in this manner is the first step in supervised pattern recognition which develops classification models when the class assignment is known. For example, the majority of observed spectral variation can be modeled by three abstract factors which are related to several physical properties including body fat, tissue hydration, and skin thickness. Categorizing subjects on the basis of these three features produces eight different classes if each feature is assigned a "high" and "low" value. The drawback of this approach is that attention is not given to spectral similarity and the number of classes tends to increase exponentially with the number of features.

Unsupervised methods rely solely on the spectral measurements to explore and develop clusters or natural groupings of the data in feature space. Such an analysis optimizes the within cluster homogeneity and the between cluster separation. Clusters formed from features with physical meaning can be interpreted based on the known underlying phenomenon causing variation in the feature space.

However, cluster analysis does not use a priori information and can yield inconsistent results.

A combination of the two approaches is applied to use a priori knowledge and exploration of the feature space for naturally occurring spectral classes. Under this approach, classes are first defined from the features in a supervised manner. Each set of features is divided into two or more regions and classes are defined by combinations of the feature divisions. A cluster analysis is performed on the data and the results of the two approaches are compared. Systematically, the clusters are used to determine groups of classes that can be combined. After conglomeration the number of final class definitions is significantly reduced according to natural divisions in the data.

Subsequent to class definition a classifier is designed through supervised pattern recognition. A model is created based on class definitions which transforms a measured set of features to an estimated classification. Because the ultimate goal of the classifier is to produce robust and accurate calibration models, an iterative approach must be followed in which class definitions are optimized to satisfy the specifications of the measurement system.

Statistical Classification

The statistical classification methods are applied to mutually exclusive classes whose variation can be described statistically (see, for example, J. Schurmann, *Pattern Classification. A Unified View of Statistical and Neural Approaches*, John Wiley & Sons, Inc., New York (1996); and J. Bezdek, S. Pal, eds., *Fuzzy Models for Pattern Recognition*, IEEE Press, Piscataway, N.J. (1992)). Once class definitions have been assigned to a set of exemplary samples, the classifier is designed by determining an optimal mapping or transformation from the feature space to a class estimate which minimizes the number of misclassifications. The form of the mapping varies by method as does the definition of optimal. Existing methods include linear discriminant analysis (see, for example, R. Duda, P. Hart, *Pattern Classification and Scene Analysis*, John Wiley and Sons, New York (1973)), SIMCA (see, for example, S. Wold, M. Sjostrom, *SIMCA: A method for analyzing chemical data in terms of similarity and analogy*, Chemometrics: Theory and Application, ed. B. Kowalski, ACS Symposium Series, 52 (1977)), k nearest-neighbor (see, for example, R. Duda, P. Hart, *Pattern Classification and Scene Analysis*, John Wiley and Sons, New York (1973)), and various forms of artificial neural networks (see, for example, S. Haykin, *Neural Networks: A Comprehensive Foundation*, Upper Saddle River, N.J., Prentice-Hall (1994); and Y. Pao, *Adaptive Pattern Recognition and Neural Networks*, Addison-Wesley Publishing Company, Inc., Reading, Ma. (1989)).

The result is a function or algorithm that maps the feature to a class, c, according to:

$$c = f(z) \quad (3)$$

where c is an integer on the interval [1,P] and P is the number of classes. The class is used to select or adapt the calibration model as discussed below in connection with calibration.

Fuzzy Classification

While statistically based class definitions provide a set of classes applicable to blood analyte estimation, the optical properties of the tissue sample resulting in spectral variation change over a continuum of values. Therefore, the natural variation of tissue thickness, hydration levels, and body fat content, among others, results in class overlap. Distinct class boundaries do not exist and many measurements are likely to fall between classes and have a statistically equal chance of membership in any of several classes. Therefore, hard class boundaries and mutually exclusive membership functions appear contrary to the nature of the target population.

A more appropriate method of class assignment is based on fuzzy set theory (see, for example, J. Bezdek, S. Pal, eds., *Fuzzy Models for Pattern Recognition*, IEEE Press, Piscataway, N.J. (1992); C. Chen, ed., *Fuzzy Logic and Neural Network Handbook*, Piscataway, N.J., IEEE Press (1996); and L. Zadeh, *Fuzzy Sets*, Inform. Control, vol. 8, pp. 338–353 (1965)).

Generally, membership in fuzzy sets is defined by a continuum of grades and a set of membership functions that map the feature space into the interval [0,1] for each class. The assigned membership grade represents the degree of class membership with "1" corresponding to the highest degree. Therefore, a sample can simultaneously be a member of more than one class.

The mapping from feature space to a vector of class memberships is given by:

$$c_k = f_k(z) \quad (4)$$

where k=1,2, . . . P, $f_k(\bullet)$ is the membership function of the kth class, $C_k \in [0,1]$ for all k and the vector $c \in \Re^P$ is the set of class memberships. The membership vector provides the degree of membership in each of the predefined classes and is passed to the calibration algorithm.

The design of membership functions use fuzzy class definitions similar to the methods previously described. Fuzzy cluster analysis can be applied and several methods, differing according to structure and optimization approach can be used to develop the fuzzy classifier. All methods attempt to minimize the estimation error of the class membership over a population of samples.

Calibration

Blood analyte prediction occurs by the application of a calibration model to the preprocessed measurement as depicted in FIG. 1. The proposed prediction system involves a calibration or set of calibration models that are adaptable or selected on the basis of the classification step. The following discussion describes the calibration system for the two types of classifiers.

Mutually Exclusive Classes

Figure 5:
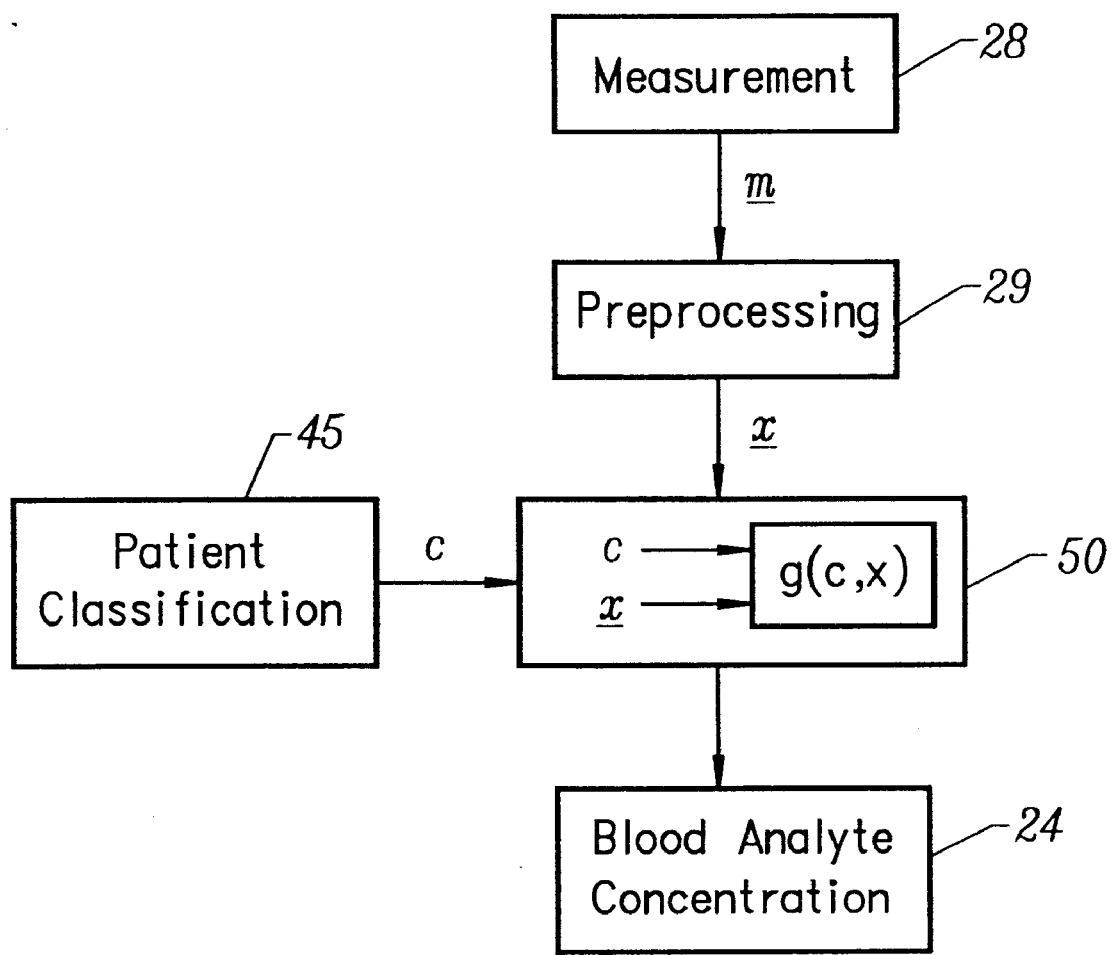
FIG. 5 is a block schematic diagram showing a general calibration system for mutually exclusive classes according to the invention.

In the general case, the designated classification is passed to a nonlinear model which provides a blood analyte prediction based on the subject classification and spectral measurement. This process, illustrated in FIG. 5, involves the modification of the estimation strategy for the current subject according to the structural tissue properties and physiological state manifested in the absorbance spectrum.

This general architecture necessitates a nonlinear calibration model 50, such as nonlinear partial least squares or artificial neural networks because the mapping is highly nonlinear. The blood analyte prediction for the preprocessed measurement x with classification specified by c is given by:

$$\hat{y} = g(c, x) \quad (5)$$

where $g(\bullet)$ is a nonlinear calibration model which maps x and c to an estimate of the blood analyte concentration, $\hat{y}$.

Figure 6:
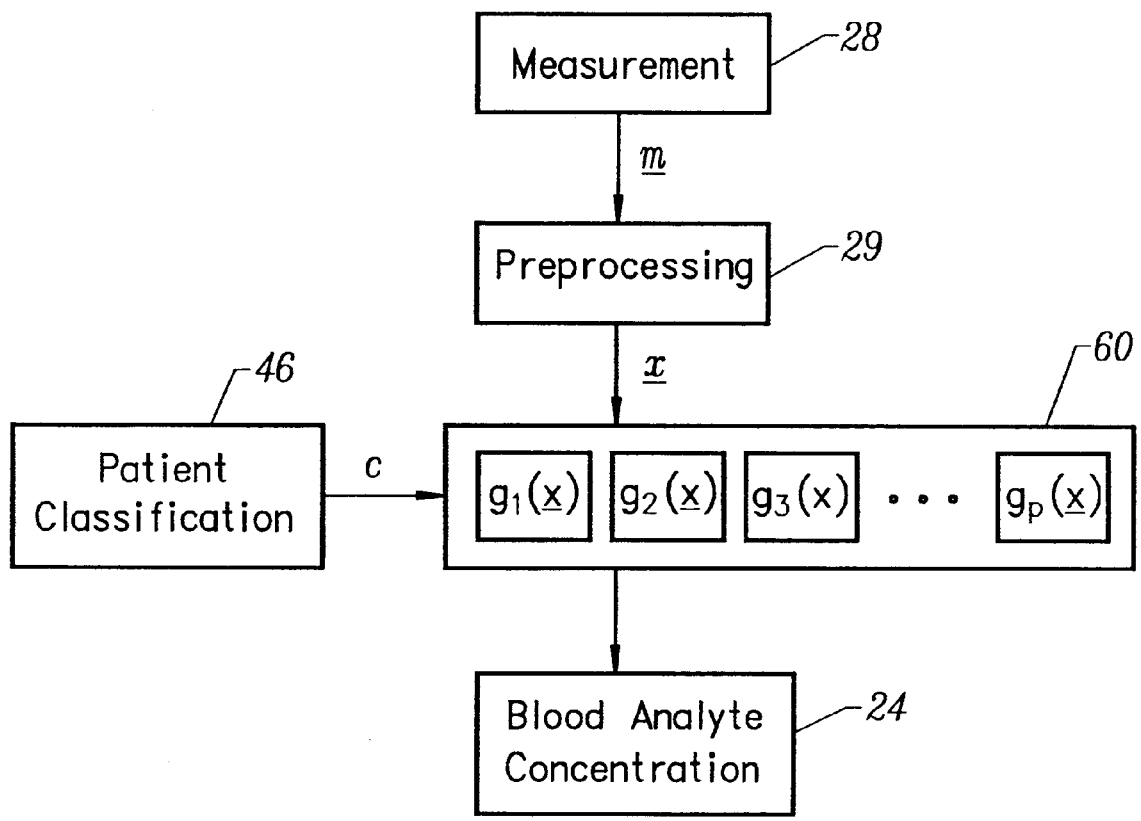
FIG. 6 is a block schematic diagram showing an example of parallel calibration models for mutually exclusive classes according to the invention.

In the preferred realization, shown in FIG. 6, a different calibration 60 is realized for each class. The estimated class is used to select one of p calibration models most appropriate for blood analyte prediction using the current measurement. Given that k is the class estimate for the measurement, the blood analyte prediction is:

$$\hat{y} = g_k(x) \quad (6)$$

where $g_k(\cdot)$ is the calibration model associated with the kth class.

The calibrations are developed from a set of exemplar absorbance spectra with reference blood analyte values and pre-assigned classification definitions. This set, denoted the "calibration set," must have sufficient samples to completely represent the subject population and the range of physiological states in the subject population. The p different calibration models are developed individually from the measurements assigned to each of the p classes. The models are realized using known methods including principal component regression (see, for example, H. Martens, T. Naes, *Multivariate Calibration,* New York, John Wiley and Sons (1989)), partial least squares regression (see, for example, P. Geladi, B. Kowalski, *Partial least-squares regression: a tutorial,* Analytica Chimica Acta, 185, pp. 1–17 (1986)), and artificial neural networks (see, for example, S. Haykin, *Neural Networks: A Comprehensive Foundation,* Upper Saddle River, N.J., Prentice-Hall (1994)).

The various models associated with each class are evaluated on the basis of an independent test set or cross validation and the best set of models are incorporated into the Intelligent Measurement System. Each class of subjects then has a calibration model specific to it.

Fuzzy Class Membership

Figure 7:
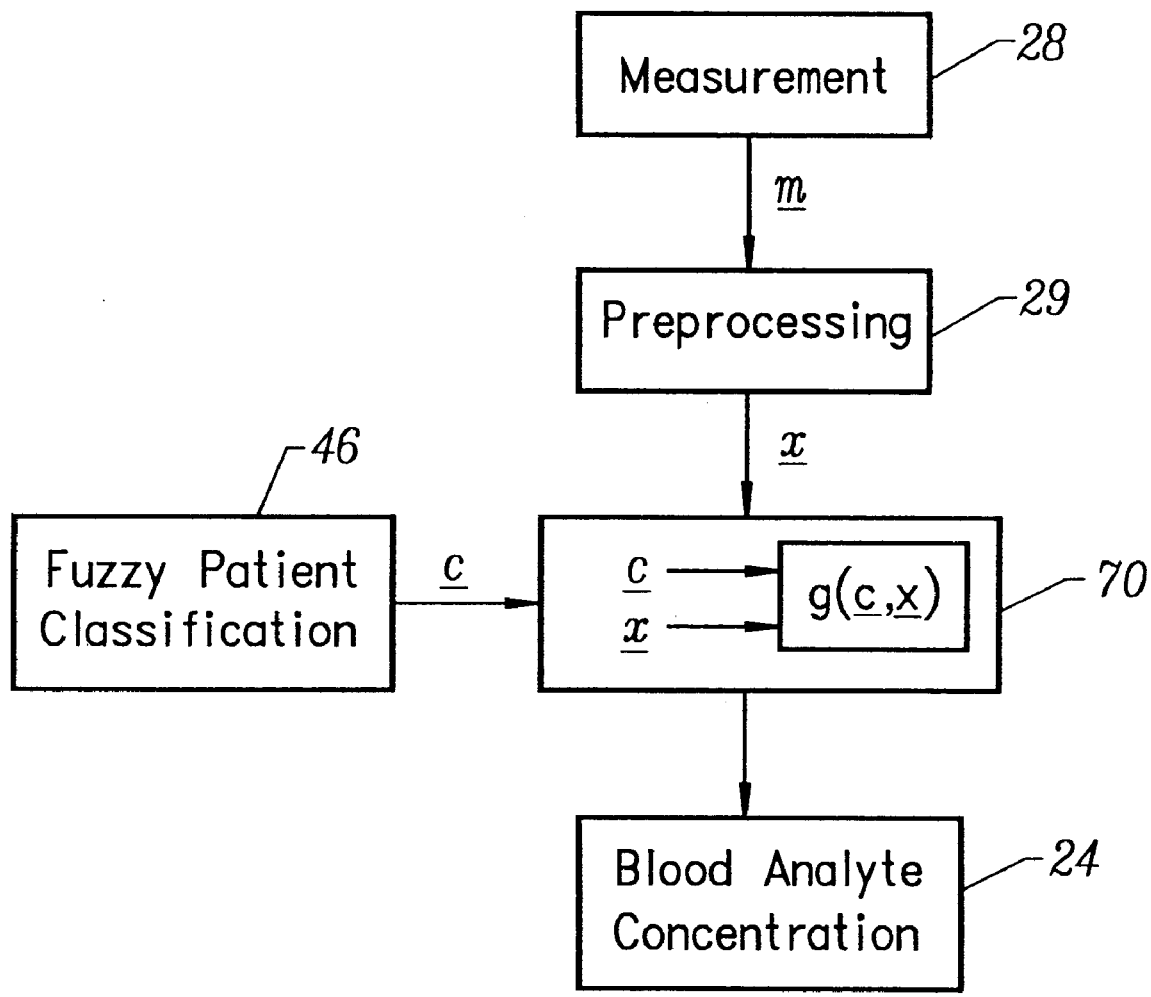
FIG. 7 is a block schematic diagram showing a general calibration system for fuzzy class assignments according to the invention.

When fuzzy classification is employed the calibration is passed a vector of memberships rather than a single estimated class. The vector, c, is used to determine an adaptation of the calibration model suitable for blood analyte prediction or an optimal combination of several blood analyte predictions. In the general case, illustrated in FIG. 7, the membership vector and the preprocessed absorbance spectrum are both used by a single calibration 70 for blood analyte prediction. The calculation is given by:

$$\hat{y}=g(c,x) \tag{7}$$

where $g(\cdot)$ is a nonlinear mapping determined through nonlinear regression, nonlinear partial least squares or artificial neural networks. The mapping is developed from the calibration set described previously and is generally complex.

Figure 8:
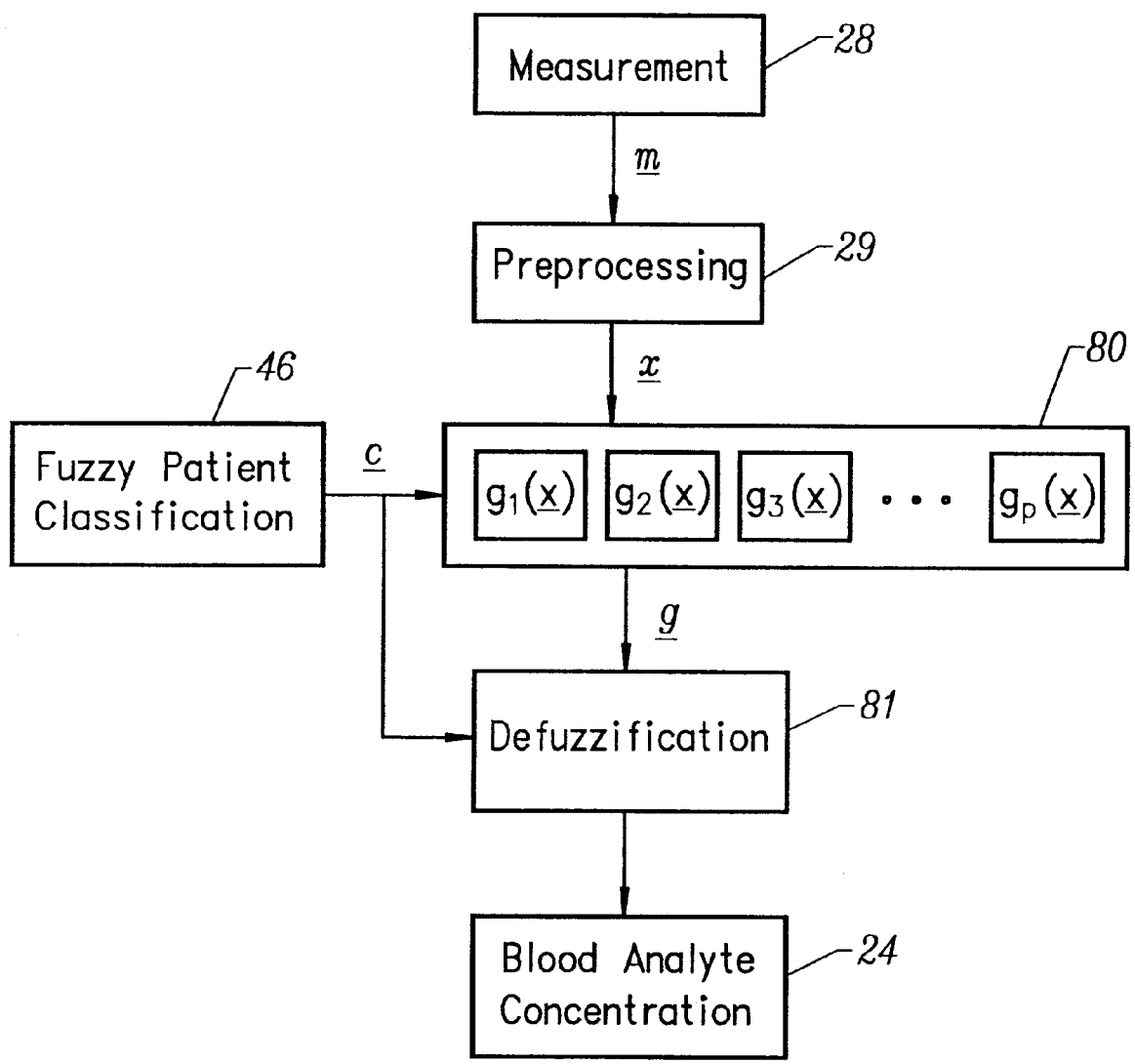
FIG. 8 is a block schematic diagram showing an example of parallel calibration models for fuzzy set assignments according to the invention.

The preferred realization, shown in FIG. 8, has separate calibrations 80 for each class similar to that shown in FIG. 6. However, each calibration is generated using all measurements in the calibration set by exploiting the membership vector assigned to each measurement. In addition, the membership vector is used to determine an optimal combination of the p blood analyte predictions from all classes through defuzzification 81. Therefore, during calibration development a given measurement of the calibration set has the opportunity to impact more than one calibration model. Similarly, during prediction more than one calibration model is used to generate the blood analyte estimate.

Each of the p calibration models of FIG. 8 is developed using the entire calibration. However, when the kth calibration model is calculated, the calibration measurements are weighted by their respective membership in the kth class. As a result, the influence of a sample on the calibration model of a particular class is a function of its membership in the class.

In the linear case, weighted least squares is applied to calculate regression coefficients and, in the case of factor based methods, the covariance matrix (see, for example, N. Draper, H. Smith. *Applied Regression Analysis,* $2^{nd}$ Ed., John Wiley and Sons, New York (1981)).

Given a matrix of absorbance spectra $X_k \in \Re^{r \times w}$ and reference blood analyte concentrations $Y \in \Re^r$ where r is the number of measurement spectra and w is the number wavelengths, let the membership in class k of each absorbance spectrum be the elements of $C_k \in \Re^r$. Then the principal components are given by:

$$F = X_k M \tag{8}$$

where M is the matrix of the first n eigen vectors of P.

The weighted covariance matrix P is determined through:

$$P = X_k V X_k^T \tag{9}$$

where V is a square matrix with the elements of $C_k$ on the diagonal.

The regression matrix, B, is determined through:

$$B = (F^T V F)^{-1} F^T V Y. \tag{10}$$

When an iterative method is applied, such as artificial neural networks, the membership is used to determine the frequency the samples are presented to the learning algorithm. Alternately, an extended Kalman filter is applied with a covariance matrix scaled according to V.

The purpose of defuzzification is to find an optimal combination of the p different blood analyte predictions, based on a measurement's membership vector that produces accurate blood analyte predictions. Therefore, defuzzification is a mapping from the vector of blood analyte predictions and the vector of class memberships to a single analyte prediction. The defuzzifier can be denoted as transformation such that:

$$\hat{y} = d(c, [y_1 y_2 y_3 \ldots y_p]) \tag{11}$$

where $d(\cdot)$ is the defuzzification function, c is the class membership vector and $y_k$ is the blood analyte prediction of the kth calibration model. Existing methods of defuzzification, such as the centroid or weighted average, are applied for small calibration sets. However, if the number of samples is sufficient, $d(\cdot)$ is generated through a constrained nonlinear model.

Algorithm Manager

The algorithm manager 10 (see FIG. 1) is responsible for reporting results to the operator, coordinating all algorithmic events, monitoring the performance based on the class, and adapting the rules as necessary. Both class estimates and blood analyte predictions are reported to the algorithm manager. The classifier also generates a measure of the certainty of class membership. If the measurement does not fit into one of the existing classes the supervisor notifies the operator that the prediction is invalid. Further spectral measurements are taken to determine if the error is due to the instrument, measurement technique or sample. This error detection and correction algorithm is used to determine if more classes are necessary or if the instrument requires maintenance.

Implementation

The following discussion describes the implementation and experimental results of two forms of the Intelligent Measurement System for Blood Analyte Prediction (IMS) that were developed for the prediction of blood glucose concentration. It will be appreciated by those skilled in the art that other forms of the invention for other purposes may be developed. In the first form, a Crisp Classification System is used to determine one of four suitable prediction models. The second realization, denoted the Fuzzy Classification System, employs fuzzy membership rules to determine the class membership in each of six classes. The outputs of the corresponding six prediction models are combined using a defuzzification procedure to produce a single blood glucose prediction.

The discussion below first describes the overall instrument containing the IMS implementations and the subsequent discussion describes the operation of the two implementations. The final discussion details experimental results obtained from a clinical study.

The two implementations are specific to the prediction of blood glucose concentration. However, the invention is appropriate for the prediction of all blood analytes and other biological and other compounds that absorb in the NIR.

Instrument Description

Figure 9:
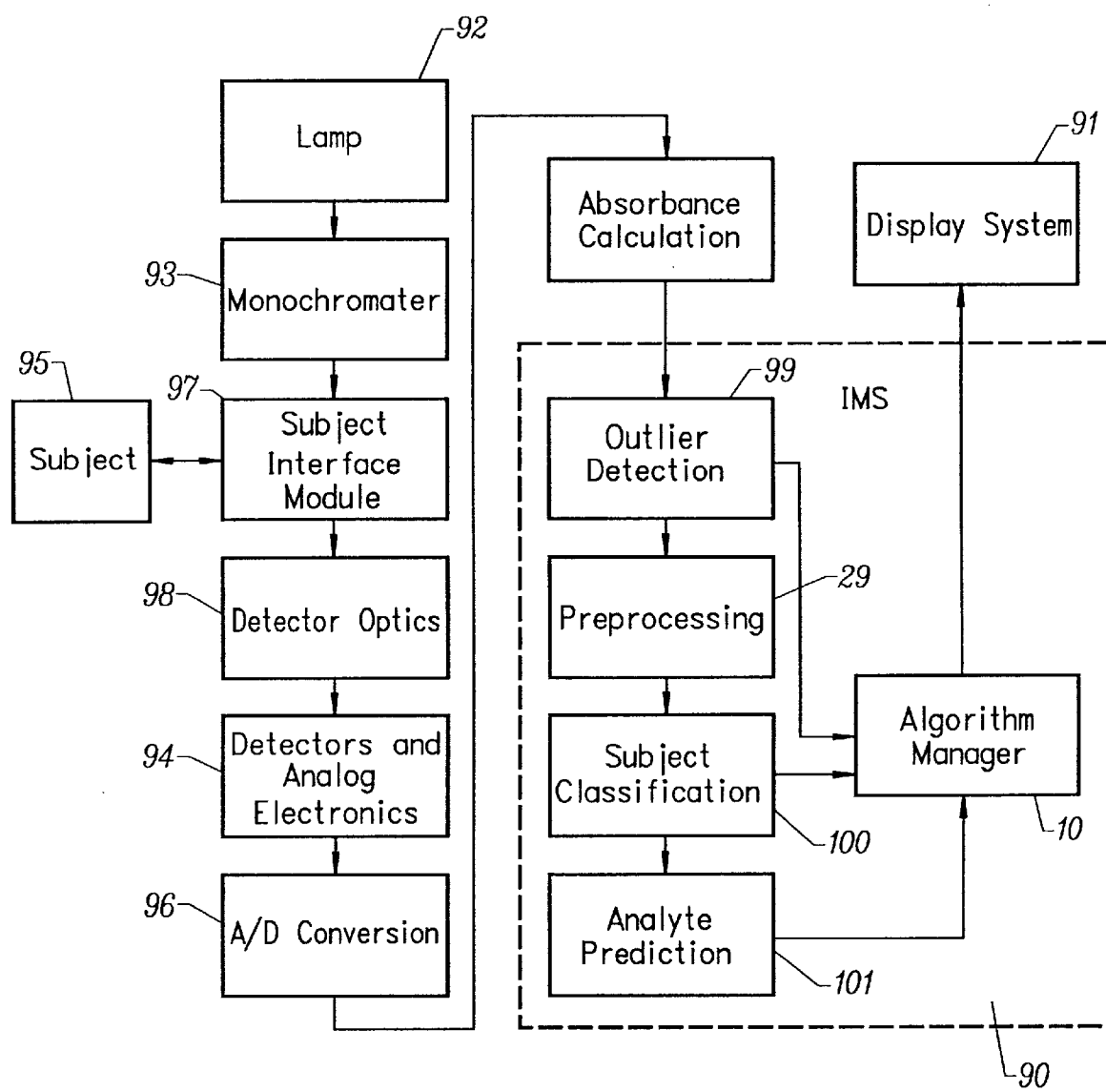
FIG. 9 is a block schematic diagram of an intelligent measurement system instrument according to the invention.

The Intelligent Measurement System is implemented in a scanning spectrometer which determines the NIR absorbance spectrum of the subject forearm through a diffuse reflectance measurement. A block diagram of the integrated instrumentation and the IMS is shown in FIG. 9 and includes the general instrument components, the IMS 90 and a display system (output device) 91. The instrument employs a quartz halogen lamp 92, a monochromater 93, a subject interface module 97, detector optics 98, and InGAs detectors 94. The detected intensity from the subject 95 is converted to a voltage through analog electronics 94 and digitized through a 16-bit A/D converter 96. The spectrum is passed to the IMS for processing and results in either a glucose prediction or a message indicating an invalid scan.

Alternately, the IMS can be employed with existing NIR spectrometers that are commercially available, including a Perstorp Analytical NIRS 5000 spectrometer or a Nicolet Magna-IR 760 spectrometer.

Crisp Classification System

Overview

Figure 10:
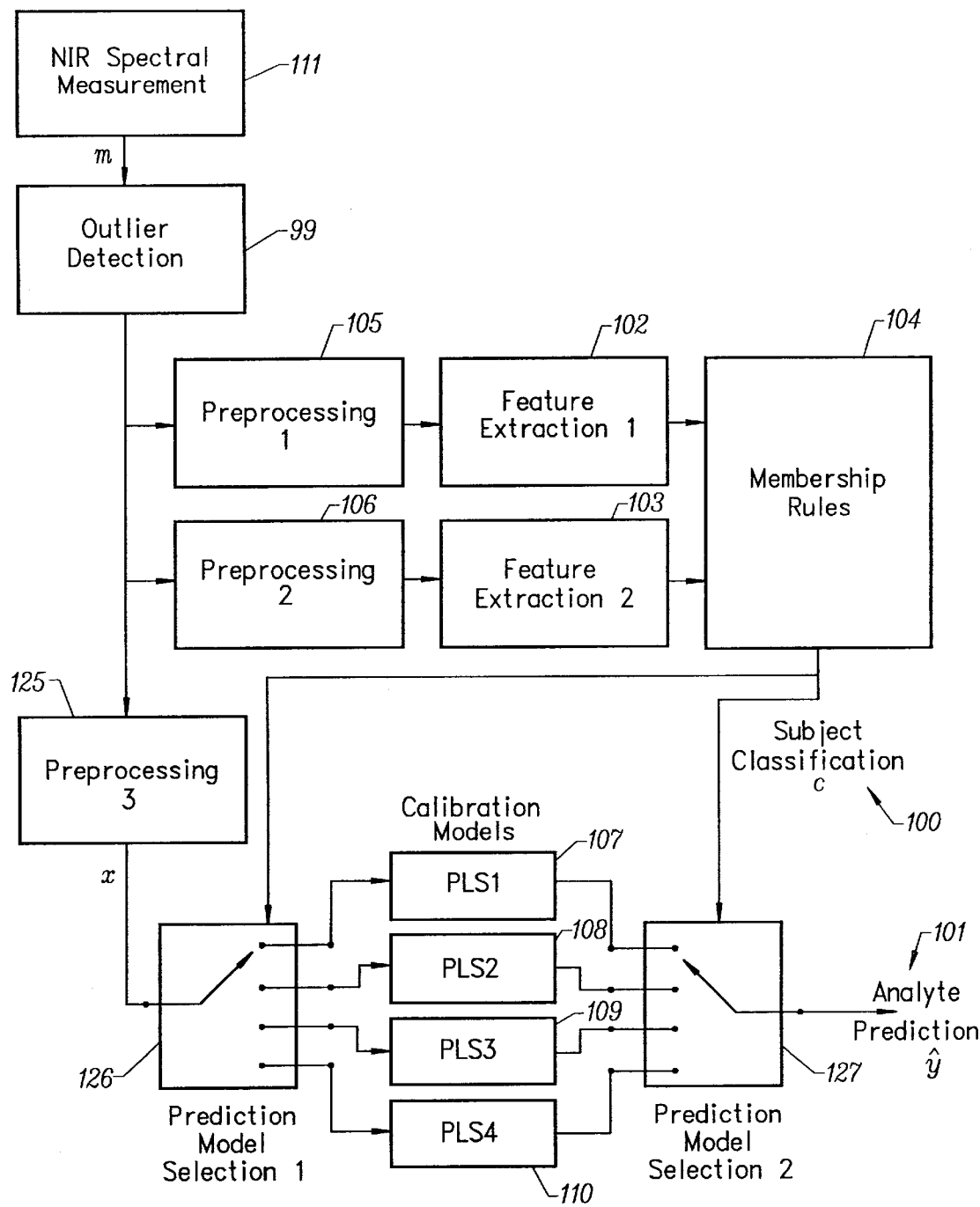
FIG. 10 is a block schematic diagram of the intelligent measurement system with crisp classification rules according to the invention.

FIG. 10 depicts an implementation of the IMS that involves subject classification through crisp or classical decision rules denoted IMS-CC. The objective of the classification is to determine which of four calibration models are applied for analyte prediction. This decision is accomplished through feature extraction 102, 103, classification 100, and application of a set of decision rules 104.

Prior to classification and calibration the measured noninvasive absorbance spectrum is subjected to an outlier detection 99 through principal components analysis (PCA). Spectra with significant deviations from the system's PCA model are designated as unsatisfactory and rejected. Features related to the subjects sex and age are extracted through factor based techniques (PCA and PLS) after preprocessing 105, 106. The features are supplied to a set of decision rules 104 that determine which one of four classes 107, 108, 109, 110 best represents the absorbance spectrum of the subject, given the current state and structure of the tissue volume sampled during the measurement. While this implementation depicts four classes, the invention extends to the number of classes and features that are necessary for glucose prediction accuracy. Additional classes, for example, may be determined based on features related to hydration, skin thickness, thickness of adipose tissue, volume fraction of blood in tissue, blood pressure, hematocrit levels and others.

The absorbance spectrum is also preprocessed (Preprocessing 1) 105 in a manner suitable for calibration. Although the present implementation contains one method of preprocessing for all calibration models, the preferred realization supplies separate preprocessing methods for each calibration model. The calibration model that is applied to the spectrum is determined based on the classification described above and the model output is the glucose prediction. The implementation shown in FIG. 10 contains four calibration models associated with the four classes. However, in the general case an arbitrary number of calibrations are used equal to the number of classes needed to represent the spectral variation of individuals using the instrument.

Detailed Description

NIR Spectral Measurement

The measured NIR spectrum m is a vector containing absorbance values evenly distributed in the wavelength range 1100–2500 nm. In the present application N=1400. An example measurement is depicted in FIG. 1.

Outlier Detection

The detection of spectral outliers is performed through a principal components analysis and an analysis of the residuals. First, the spectrum m is projected onto seven eigenvectors, contained in the matrix o, that were previously developed through a principal components analysis (on a calibration set of exemplary absorbance spectra) and are stored in the IMS-CC. The calculation is given by:

$$xpc_o = \sum_{k=1}^{7} mo_k \tag{12}$$

and produces the 1 by 7 vector of scores, $xpc_o$ where $o_k$ is the kth column of the matrix o. The residual q is determined according to:

$$q = m - xpc_o o^T \tag{13}$$

and compared to three times the standard deviation of the expected residual (of the a calibration set). If greater, the sample is reported by the algorithm manager to be an outlier.

Processing 1 and Feature Extraction 1

The first feature is the result of a classification of the subject into male and female categories and involves spectral preprocessing, decomposition through principal components analysis, and classification through linear discriminant analysis. The feature is not a determination of the subject's sex but rather provides a measure of the tissue volume sampled as compared to that of other subjects.

Figure 11:
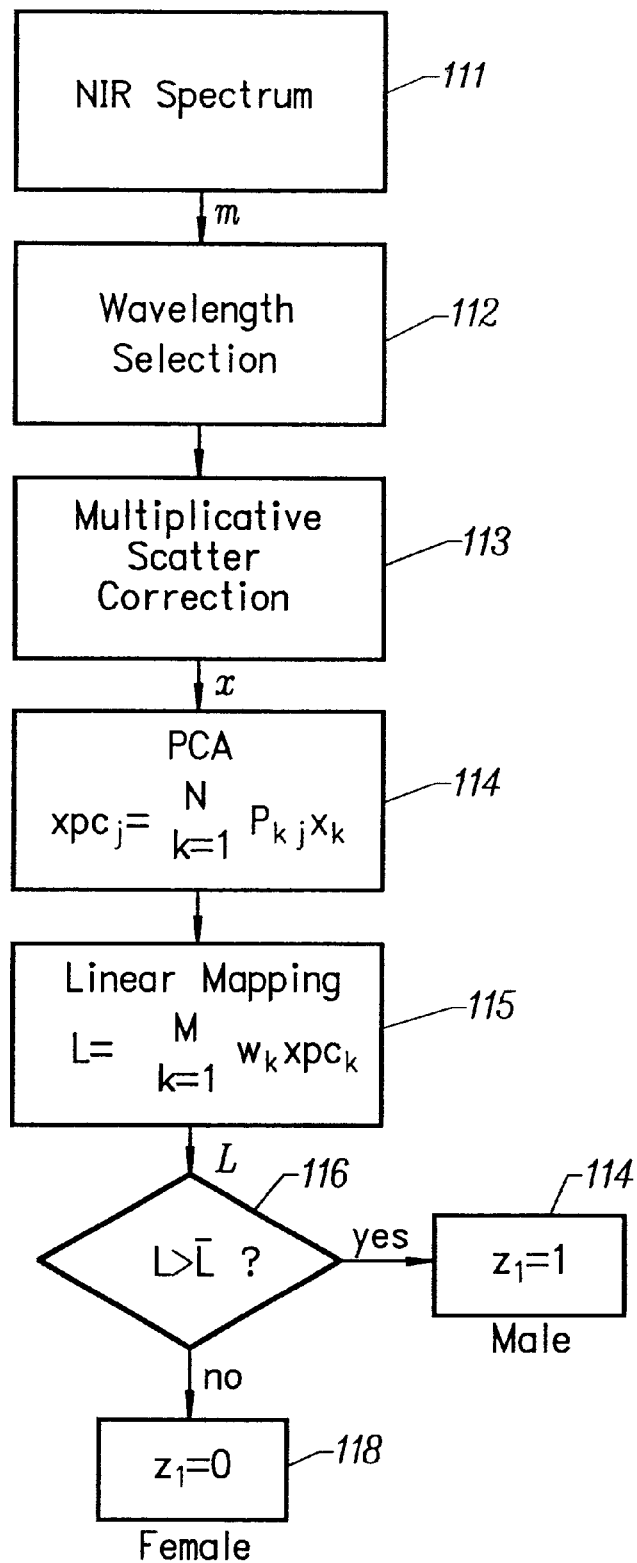
FIG. 11 is a flow diagram showing processing steps for preprocessing 1 and feature extraction 1 of FIG. 10, according to the invention.

The process, depicted in FIG. 11, receives the absorbance spectrum m from the outlier detection system 111. Wavelength selection 112 is applied to truncate the spectral range to regions with significant absorption due to fat in adipose tissue (1100 to 1400 nm). The spectrum is next processed through multivariate scatter correction 113 (see P. Geladi, D. McDougall, H. Martens, *Linearization and Scatter-Correction for Near-Infrared Reflectance Spectra of Meat,* Applied Spectroscopy, vol. 39, pp. 491–500, 1985) through a rotation that fits it to the expected or reference spectrum $\bar{m}$ contained in the Intelligent System and determined from a prior set of examplary samples. First, the spectrum is fit via linear regression according to:

$$m = a + b\bar{m} + e \tag{14}$$

where a and b are the slope and intercept and e is the error in the fit. The spectrum is then corrected through:

$$x = (m-a)/b \tag{15}$$

where x is the processed absorbance spectrum. The processed spectrum is projected onto the eigenvectors, $p_k$, that were previously developed through a principal components analysis 114 (on a calibration set of exemplary absorbance spectra) and are stored in the IMS-CC. The calculation, shown in FIG. 11, produces the 1 by N vector of scores, xpc.

A discriminant function is applied to classify the subjects on the basis of the first M scores (M=5 is this application).

The scores are rotated through a cross product with the discriminant, w, as depicted in FIG. 11 to produce the scalar, L (115). This result is compared 116 to $\overline{L}$, the center between the two classes. If L>$\overline{L}$ then the subject is classified as a female 118 and the feature $z_1=1$. If not, the spectrum is classified as belonging to a male 117 and $z_1=0$.

Processing 2 and Feature Extraction 2

Figure 12:
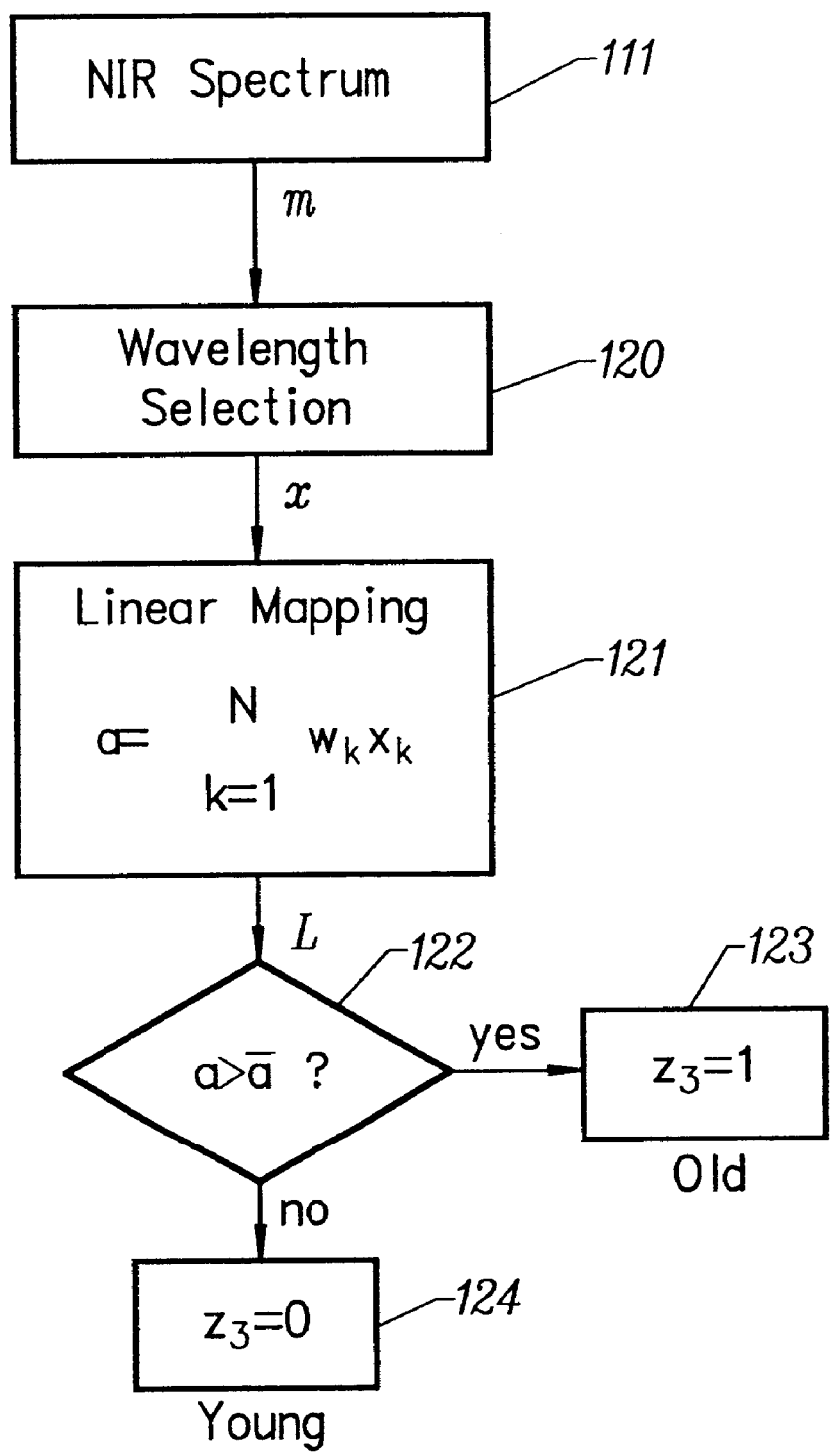
FIG. 12 is a flow diagram showing processing steps of preprocessing 2 and feature extraction 2 of FIG. 10, according to the invention.

The second feature extraction process 103 (see FIG. 10) is represented in FIG. 12 and involves the prediction of the subject's age using a linear model developed through partial least squares regression (PLS). First, the wavelength range is truncated 120 to the 1100 to 1800 nm region. Next, the subject's age is predicted through a calibration model that is part of the IMS-CC. The model, developed through PLS on a calibration set of exemplary samples, consists of a set of coefficients contained in the vector w and is applied as shown in FIG. 12 to produce the age prediction a 121. The subject is classified as "young" or "old" by comparing a to the mean age $\overline{a}=49$ as detailed in FIG. 12, see 122. The result of the classification is the calculated feature, $z_2$, which assumes vales of zero or one corresponding to a classification of "old" 123 or "young" 124 respectively.

Membership Rules

The membership rules 104, shown in FIG. 13, determine the appropriate calibration model to predict the blood glucose concentration from the measured absorbance spectrum. Based on the two features, $z_1$ and $z_2$, four classes are possible. The consequence of the decision it the selection of one of four calibration models to use to predict the blood glucose concentration denoted PLS1–4.

This classification based on spectral data and not the obvious observation of the subject is necessary because it is indicative of the state of the subject's tissue. For example, a classification of "old" indicates that the subject's spectrum appears similar to the spectra previously gathered from older individual's. The results reflect gross spectral properties that are correlated to age but not necessarily deduced based on the actual chronological age.

Preprocessing 3

The absorbance spectrum is processed specifically for calibration through MSC as described above and a 31-point Savisky-Golay first derivative in the form of a finite impulse response filter 125 (see A. Savitzky, M. Golay, *Smoothing and Differentiation of Data by Simplified Least Squares Procedures*, Anal. Chem., vol. 36, no. 8, pp. 1627–1639, 1964). The result is mean-centered by subtracting, $\overline{x}$, the mean processed absorbance spectrum from a calibration set of exemplary samples that is stored in the IMS-CC. Wavelength selection is performed to include the following wavelengths: 1100–1350 nm, 1550–1750 nm and 2050–2375 nm.

Prediction Model Selection 1–2

Based on the subject's classification, one of the four calibration models is selected for application as depicted in the two selectors 126, 127 of FIG. 10.

Calibration Models PLS1, PLS2, PLS3, PLS4

The four calibration models 107–110 each consist of a 1×N vector of coefficients that map x to a prediction of glucose. Each set of coefficients was developed using samples (from a calibration set) that were classified as belonging to its associated class. Therefore, the models are limited to predicting glucose concentration levels on subjects that are classified in their respective classes.

Given the processed spectrum, x, the classification, c, and the model coefficients $w_c$ associated with c, the blood glucose prediction is given by:

$$\hat{y} = \sum_{k=1}^{N} w_{c,k} x_k \quad (16)$$

were $w_{c,k}$ is the kth element of $w_c$.

Fuzzy Classification System

Overview

While the classification system based on distinct class boundaries shown in FIG. 10 provides a set of classes applicable to blood analyte estimation, the optical properties of the tissue sample vary over a continuum of values. Distinct class boundaries do not exist and many measurements are likely to fall between classes and have a statistically equal chance of membership in any of several classes. Therefore, hard class boundaries and mutually exclusive membership functions appear contrary to the nature of the target population.

Figure 14:
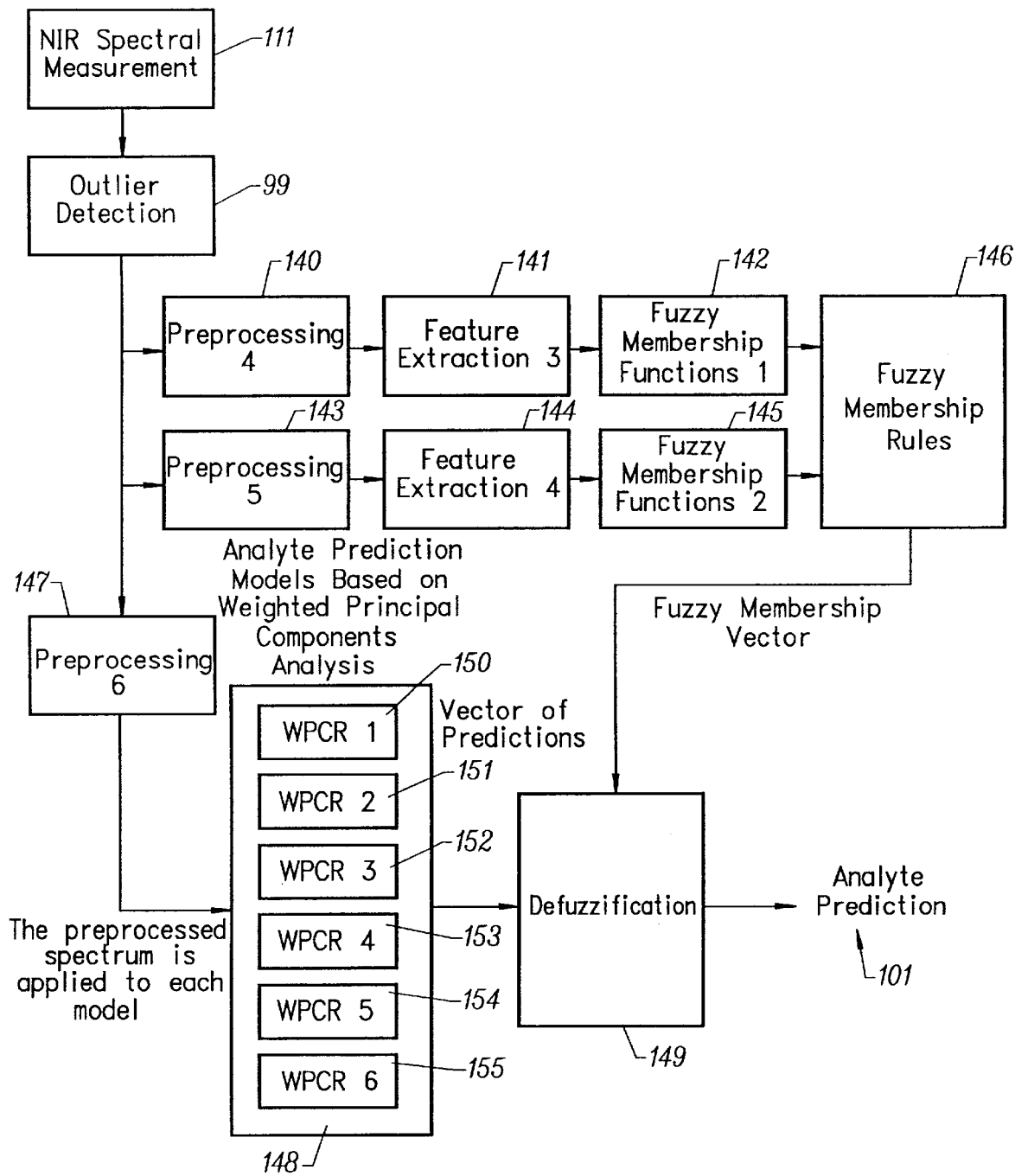
FIG. 14 is a block schematic diagram of an intelligent measurement system with fuzzy classification according to the invention.

The system shown in FIG. 14, denoted the IMS-FC, employs fuzzy sets to define a continuum of grades in each of the classes. Rather than categorizing subjects into distinct and independent groups, this system determines the degree of membership of a particular subject in each of six classes (150–155). Therefore, each subject shares membership in every class and each of the parallel calibration models has the opportunity to contribute to the prediction of the blood analyte based.

The weighted combination (based on class membership) of the prediction of all calibration models in the system produces an apparent continuum of calibration models. Subjects falling mid-point between two classes, for example, are predicted using both rather than one of the two (calibration models) and produce a prediction with a greater level of confidence. Similarly, the calibrations are created through a weighted principal components regression (WPCR) and are not exclusive to a distinct population.

Similar to the IMS-CC, the fuzzy system (IMS-FC) classifies exclusively on the basis of spectral information. The measured absorbance spectrum is preprocessed for feature extraction. The features in this implementation are continuous (calculated) variables related to the absorption of body fat that is manifested spectrally and the apparent age of the sampled tissue volume. Fuzzification occurs through a set of membership functions that produce five membership values associated with the sub-sets male, female, young, middle aged and old. These membership values are transformed through decision rules 146 to produce the degree of class membership in each of six classes.

The spectrum is also preprocessed in a manner suitable for calibration and applied to each of the six calibration models. The results (six blood glucose estimates) are combined through the process of defuzzification 149 in which the degree of class membership is used to weight the influence of each prediction.

While the present implementation involves a specific number of features, classes, decision rules and calibrations models, the invention may use an arbitrary number of each in the configuration shown to produce a blood analyte predictions. Further, the invention covers the use of fuzzy classification for the purpose of blood analyte prediction or other analytes determinations.

Detailed Description

NIR Spectral Measurement

The measured NIR spectrum, m, 111 is a vector containing absorbance values evenly distributed in the wavelength range 1100–2500 nm. In the present application N=1400 and an example measurement is depicted in FIG. 1.

Outlier Detection

The detection 99 of spectral outliers is performed through a principal components analysis and an analysis of the residuals. First, the spectrum m is projected onto seven eigenvectors, contained in the matrix o that were previously developed through a principal components analysis on a calibration set and stored in the IMS-FC. The calculation is given by:

$$xpc_o = \sum_{k=1}^{7} mo_k \qquad (17)$$

and produces the 1 by 7 vector of scores, $xpc_o$ where $o_k$ is the kth column of the matrix o. The residual, q, is determined according to:

$$q = m - xpc_o o^T \qquad (18)$$

and compared to three times the standard deviation of the expected residual determined from a calibration set. If greater, the sample is reported by the algorithm manager to be an outlier.

Processing 4 (140) and Feature Extraction 3 (141)

Figure 15A:
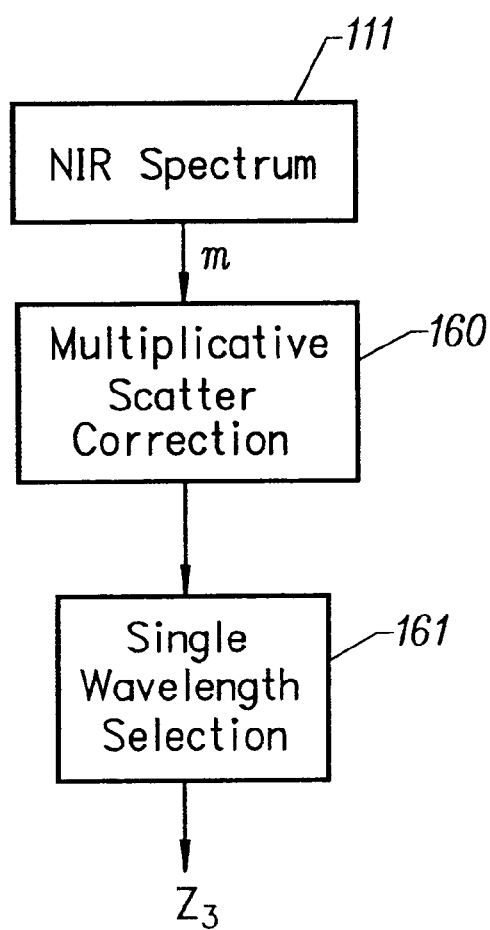
FIG. 15 is a flow diagram showing preprocessing a feature extraction processes for the fuzzy classification system shown in FIG. 14, according to the invention.

The first feature for the IMS-FC is related to the fat stored in adipose tissue as manifested through absorption bands in the 1100–1380 nm range. This feature is extracted, as shown in FIG. 15A, by performing multiplicative scatter correction 160 (described previously) on the 1100–1380 nm range. The absorbance value corresponding to the wavelength 1208 nm 161 is the value of the feature, $z_3$, associated with the measured absorbance spectrum.

Processing 5 (143) and Feature Extraction 4 (144)

Figure 15B:
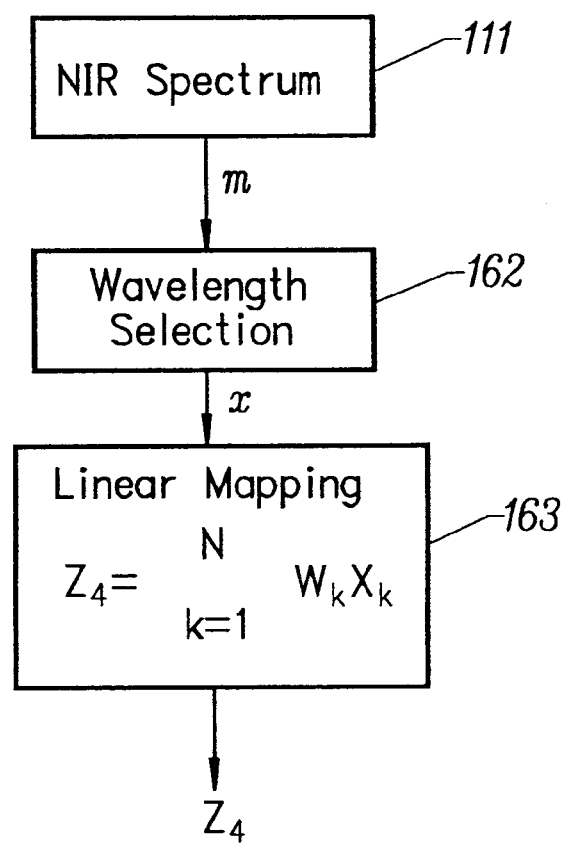

The second feature extraction, shown in FIG. 15B, produces a prediction of the subject's age based on the measured absorbance spectrum. First, the wavelength range is truncated to the 1100 to 1800 nm region 162. Next, the subject's age is predicted through a calibration model 163 that is part of the IMS-FC. The model, developed through PLS on a calibration set of representative samples, consists of a set of coefficients contained in the vector w and is applied as shown in FIG. 12 to produce the age prediction $z_4$.

Fuzzy Membership Functions

The fuzzy membership functions 142, 145 are used to determine the degree of membership of the subject in specific sub-sets that are later combined through the decision rules. Each membership function maps the feature input to a value between 0 and 1 through a gaussian function. The general equation employed to represent the membership functions is:

$$y = e^{\frac{-1}{2\sigma^2}(z-\bar{z})^2} \qquad (19)$$

where y is the degree of membership in a sub-set, z is the feature used to determine membership, $\bar{z}$ is the mean or center of the fuzzy sub-set and $\sigma$ is the standard deviation.

Figure 16:
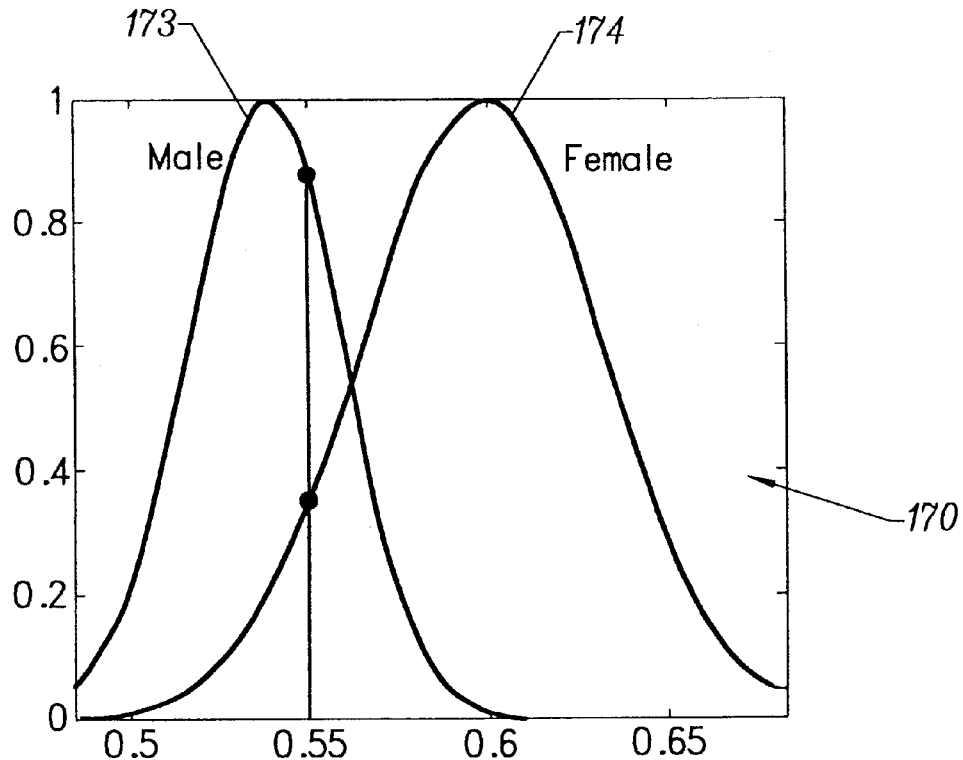
FIG. 16 provides a pair of graphs that plot the membership function for the fuzzy classification system of FIG. 14, where two features are used to determine the degree of membership in the sex and age related sub-sets, according to the invention.
Figure 16:
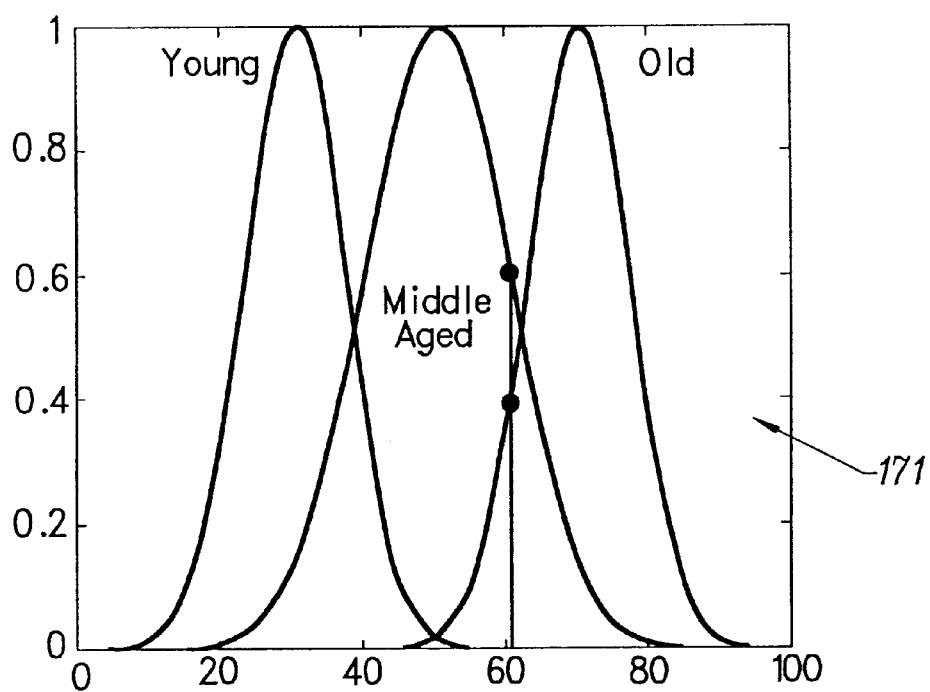

In FIG. 16, two broad sets are used that are denoted Membership Functions 1 (142) and Membership Functions 2 (145). Membership Functions 1 represent the subject's sex 170 using two sub-sets (male 173 and female 174). Membership Functions 2 uses three subsets, described below, to represent the age 171 of the subject. The degree of membership in each sub-set is calculated through Equation (15) and used through fuzzy operators and decision rules to assign class membership.

The first set of membership functions 170, shown in FIG. 16 (top), are gaussian functions that determine the degree of membership in the male and female sub-sets based on the feature related to the absorption of fat (Feature 3). The mean and standard deviation associated with each sub-set (and used with Equation 15) were determined from a large population of subjects and are listed in Table 1. As shown in the figure, the greater z the more likely the subject falls into the category of females. Conversely, lower values of z give lower membership in the category of females and higher in the category of males.

The second set of membership functions 171, shown in FIG. 16 (bottom), are gaussian functions that determine the degree of membership in the categories young, middle aged and old based on the feature representing the prediction of age (Feature 4). The mean and standard deviation associated with each of the three categories were determined qualitatively based on inspection of a target population of subjects and are listed in Table 2.

TABLE 1

Parameters for the Membership Functions 1 plotted in FIG. 16

| Subset Category | Mean(AU) | Standard Deviation (AU) |
|---|---|---|
| Females | 0.6 | 0.03 |
| Males | 0.54 | 0.02 |

TABLE 2

Parameters of Membership Functions 2 plotted in FIG. 16

| Subset Category | Mean (Years) | Standard Deviation (Years) |
|---|---|---|
| Young | 30 | 7 |
| Middle Aged | 50 | 10 |
| Old | 70 | 7 |

Values for the feature inputs to the membership functions that are unusually high or low fall outside that expected range of the sub-sets and are assigned low membership values. This information is provided to the algorithm manager and indicates that the subject belongs to a class for which a calibration model has not been constructed. For the current implementation when y<0.1 for all sub-sets the prediction is assigned a low confidence level.

The membership functions described have been designed for a specific population of subjects and cannot be generalized to all potential individuals. The invention, however, covers the arbitrary use of membership functions to assign a degree of membership in a given class to a subject for blood analyte prediction.

Other sub-sets, for example, include the level of hydration, skin thickness, thickness of adipose tissue, volume fraction of blood in tissue, blood pressure, and hematocrit levels. The number of sub-sets per general set can also be increased arbitrarily depending on the necessarily level of discrimination for the accurate prediction of blood analytes.

Fuzzy Decision Rules

The output of Membership Functions 1 and Membership Functions 2 are two and five membership values, respectively, that are associated with the sex and age related sub-sets. The decision rules 146 are a set of operators and inferences that combine the membership values of the sub-sets into the class membership used for blood glucose prediction. The specific rules, given in Error! Reference source not found., are all possible combinations of the sub-sets described previously. The rules employ the fuzzy "and" operator which is implemented by determining the minimum of the two sub-set membership values comprising its antecedent.

As an example of the class membership assignment process assume that a subject was determined to have values for features 3 and 4 of 0.55 AU and 60 years respectively. From FIG. 16, the membership values in the male and female sub-sets are approximately 0.82 and 0.3 respectively. Similarly, the membership values for the young, middle aged and old sub-sets are 0, 0.6 and 0.35. From the rules in FIG. 17 the following class membership values are calculated:

1. If Male AND Young=min(0.82, 0.0)=0.0
2. If Male AND Middle Aged=min(0.82, 0.6)=0.6
3. If Male AND Old=min(0.82, 0.35)=0.35
4. If Female AND Young=min(0.3, 0.0)=0.0
5. If Female AND Middle Aged=min(0.3, 0.6)=0.3
6. If Female AND Old=min(0.3, 0.35)=0.3

The class membership vector, d, is given by:

$$d = [0.0\ 0.6\ 0.35\ 0.0\ 0.3\ 0.3] \quad (20)$$

and is supplied to the defuzzification block for aggregation of the predicted glucose concentrations.

The consequent listed is the calibration model that is associated with each class. In the example, the second calibration model (WPCR2) 151 was created using spectra most similar to the measured spectrum. However, the measured spectrum also has membership in the third, fifth, and sixth classes. The degree of membership in the classes is used subsequently to determine the combination of calibration models for blood analyte prediction.

Preprocessing 6 (147)

The absorbance spectrum is processed specifically for calibration through MSC as described above and a 31-point Savisky-Golay first derivative in the form of a finite impulse response filter (see A. Savitzky, M. Golay, *Smoothing and Differentiation of Data by Simplified Least Squares Procedures,* Anal. Chem., vol. 36, no. 8, pp. 1627–1639, 1964). The result is mean-centered by subtracting, $\bar{x}$, the mean processed absorbance spectrum that is stored in the IMS-FC and was determined from a calibration set. Wavelength selection is performed to include the following wavelengths: 1100–1350 nm, 1550–1750 nm and 2050–2375 nm.

Calibration

The calibration process in FIG. 14 involves the prediction of the blood analyte using all of the calibration models. Therefore, the calibration block represents a single input-multiple-output operation that produces six blood analyte predictions. The six calibration models each consist of a 1×N vector of coefficients that map x to a prediction of the blood glucose concentration. Each set of coefficients was developed using all samples in a population (the calibration set of exemplary samples). However, each calibration sample was weighted using weighted principal components regression as described in Equations 8–10. Therefore, the models are associated with the six classes.

Given the processed spectrum, x, and the model coefficients, $w_c$, associated with class c, the blood glucose prediction for the cth model is given by:

$$\hat{y}_c = \sum_{k=1}^{N} w_{c,k} x_k \quad (21)$$

were $w_{c,k}$ is the kth element of $w_c$.

Defuzzification

Figure 18:
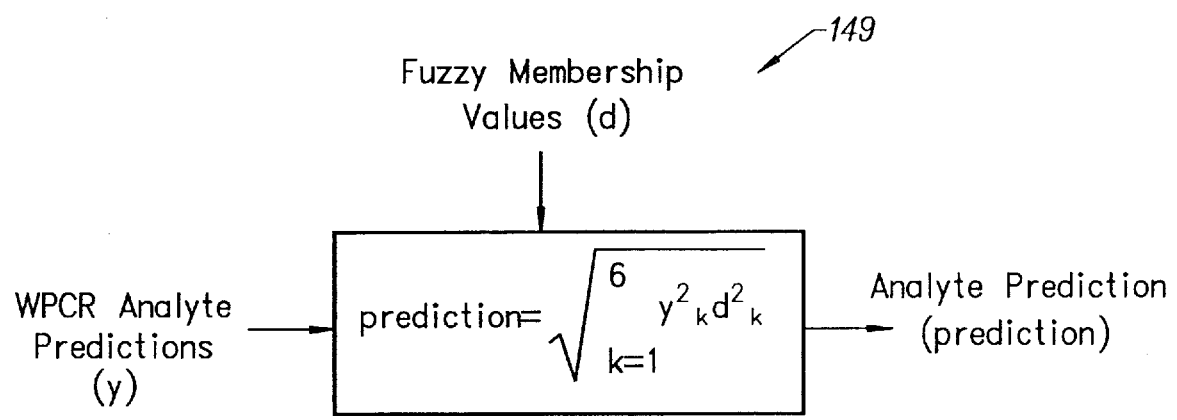
FIG. 18 is a block schematic diagram showing the defuzzification process according to the invention.

Defuzzification 149 is used to aggregate the multiple predictions into one through the degree of class membership. Prior to defuzzifying, the vector of class membership values d is normalized to unit length. The defuzzification process is shown in FIG. 18 and results in a prediction that is influenced the most by the calibration prediction associated with the class with the high degree of class membership.

The present implementation heavily biases the prediction in favor of the calibration model output with the highest degree of class membership. However, other implementations are also suggested by the invention (i.e. a simple average of all predictions or the average of all predictions corresponding to a membership value greater than a specified value).

Experimental Results

Overview

A study was performed to demonstrate the feasibility and performance of the two implementations (IMS-CC and IMS-FC). Diabetic subjects were scanned throughout the study and blood draws were taken to determine reference blood glucose concentrations. The subjects were separated at random into calibration and test sets to build and test the calibration models respectively. A standard (PLS) calibration was performed for the purpose of comparison. Finally, the performance of the two implementations was tested and compared to the standard calibration.

Experiment

Diabetic subjects (266) of diverse age, sex, and ethnicity were recruited at a local diabetic care facility and detailed demographic information about each participant was recorded. Four replicate absorbance spectra were measured on each subject's forearm and the number of samples per participant was limited to one. Venous blood draws, taken concurrently, were analyzed chemically via a hexakinase enzymatic method by an independent blood laboratory to determine reference glucose concentrations. The mean glucose concentration of the population was 120 mg/dL and the standard deviation 50 mg/dL.

The data was divided into calibration and test sets using random selection. The calibration set was used to construct the models necessary for classification and calibration in FIG. 10 and FIG. 14. The test set was applied to the constructed systems and used to evaluate for evaluation.

Results

Standard Calibration

For the purpose of comparison, a standard PLS calibration was developed and evaluated on the data after outlier analysis and preprocessing. The (PCA q-residual) outlier analysis was performed as described above and 36 samples were removed due to unusually high residuals. The absorbance spectrum was processed through MSC and a 31-point Savisky-Golay first derivative. The result was mean-centered by subtracting the mean spectrum of the calibration set from both the calibration and test sets.

PLS was applied to the calibration set and the number of factors (20) was selected by optimizing the prediction error through crossvalidation (leave-one-out). The final PLS calibration model was constructed using all calibration samples and 20 factors. The calibration model was applied to both the calibration and test sets and the results listed in Table 3.

TABLE 3

Prediction results comparing the Intelligent Measurement System to standard calibration methods. IMS-CC corresponds to the system with crisp classification (FIG. 10). IMS-FC includes fuzzy classification (FIG. 14).

| | Test Set Results | | | Calibration Set Results | | |
|---|---|---|---|---|---|---|
| Method of Prediction | Relative Error (Percent) | Standard Error of Prediction (mg/dL) | Correlation Coefficient | Relative Error (Percent) | Standard Error of calibration (mg/dL) | Correlation Coefficient |
| PLS | 262 | 43.9 | 0.48 | 26.2 | 43 | 0.53 |
| IMS-CC | 23.6 | 35.2 | 0.72 | 20.2 | 33.4 | 0.75 |
| IMS-FC | 19.7 | 30.5 | 0.8 | 18.4 | 29.5 | 0.82 |

Crisp Classification.

The outliers described in the prior section were removed and the calibration set was used to determine the parameters, eigenvectors and calibration models of the structure in shown in FIG. 10. This includes the eigenvectors (o) for the outlier analysis, the mean spectrum for MSC, the eigenvectors (p) and discriminant function (w) shown in FIG. 11, the age calibration (w) of FIG. 12, and the mean spectrum for MSC in Preprocessing 3 of FIG. 10.

The calibration set was then classified using the membership rules of FIG. 13 and separated into four individual subsets. A calibration model was developed for each subset or class corresponding to calibration models PLS1–4 in FIG. 10. Each calibration model was developed through PLS and factor selection was performed through cross validation on the calibration set.

The constructed IMS-CC was applied to the calibration and test sets and the results are listed in Table 3. The test set performance is seen to improve markedly over the base calibration indicating a performance improvement due to the system of prediction.

Fuzzy Classification

The outliers described in the prior sections were removed and the calibration set was used to determine the parameters, eigenvectors and calibration models of the structure in shown in FIG. 14. This includes the eigenvectors (o) for the outlier analysis, the mean spectrum for MSC in FIG. 15A, the age calibration (w) of FIG. 15B and the mean spectrum for MSC in Preprocessing 3 of FIG. 10. The membership functions and all other parameters described in the Fuzzy Classification System Section were applied.

The calibration set was then classified using the membership functions and rules of FIG. 16 and FIG. 17 to produce a vector of class membership values for each sample in the calibration set. The six calibration models shown in FIG. 14 were developed using Equations 8–10 (weighted principal component regression). Each of the six calibration models was optimized through cross validation on the calibration set and the final model was produced using all calibration set samples and the optimal number of factors.

The constructed IMS-FC was applied to the calibration and test sets and the results are listed in Table 3. The test set performance is seen to improve markedly over both the base calibration and the IMS-CC system indicating a performance improvement due to the use of a fuzzy classification system.

Discussion

The results in Table 3 demonstrate an improvement over the standard PLS model in accuracy, precision and significance. In addition, the IMS employing a fuzzy classification system (IMS-FC) was shown to outperform the IMS that used a crisp system. Since the IMS-FC used six classes as opposed to the four used by IMS-CC the results do not provide a final judgement regarding the performance of crisp versus fuzzy systems. However, when the number of data points is limited and the dimensionality of the problem great, the number of models that can be generated by IMS-CC is limited since an increase in classes causes a decrease in the data used to perform the calibrations associated with the classes. The IMS-FC does not share this limitation to the same extent since all samples are used to create the calibration models.

Finally, while the benefit of the IMS has been demonstrated further improvement in the results are necessary prior to application in a product. The main areas of necessary improvement are in the noise and stability of the instrument, the interface to the participant and the number of available samples for calibration.

Although the invention is described herein with reference to the preferred embodiment, one skilled in the art will readily appreciate that other applications may be substituted for those set forth herein without departing from the spirit and scope of the present invention. Accordingly, the invention should only be limited by the Claims included below.

What is claimed is:

1. A method for compensating for covariation of spectrally interfering species, sample heterogeneity, state variations, and structural variations, comprising the steps of:

providing an intelligent pattern recognition system that is capable of determining calibration models that are most appropriate for a subject at the time of measurement;

developing said calibration models from the spectral absorbance of a representative population of subjects that have been segregated into classes;

defining said classes on the basis of structural and state similarity, wherein variation within a class is small compared to variation between classes;

classifying said subject, wherein classification occurs through extracted features of a tissue absorbance spectrum related to current subject state and structure; and applying a combination of one or more of said calibration models.

2. The method of claim 1, further comprising the step of:

defining subpopulations or classes of subjects whose structure and state produce similarly featured NIR absorbance spectra;

wherein said classes have improved homogeneity leading to a reduction in variation related to optical properties and composition of a sample.

3. An intelligent system for measuring blood analytes noninvasively by operating on a near infrared (NIR) absorbance spectrum of in vivo skin tissue, said system comprising:
- a pattern classification engine for adapting a calibration model to the structural properties and physiological state of a subject as manifested in said NIR absorbance spectrum; and
- means for reducing spectral interference by applying calibration schemes specific to general categories of subjects that have been segregated into classes;
- wherein a priori information about primary sources of sample variability is used to establish said general categories of subjects.

4. The system of claim 3, wherein said pattern classification engine applies a classification rule that assumes that said classes are mutually exclusive; and wherein said pattern classification engine applies specific calibration models to said general subject categories.

5. The system of claim 3, wherein said pattern classification engine uses fuzzy set theory to develop calibration models and blood analyte predictions; wherein each calibration sample has an opportunity to influence more than one calibration model according to its class membership; and wherein predictions from more than one calibration are combined through defuzzification to produce a final blood analyte prediction.

6. The system of claim 3, further comprising:
- means for measuring blood analytes noninvasively over a diverse population of subjects at various physiological states;
- said pattern classification engine classifying subjects according to their state and structure; and
- said means for reducing spectral interference by applying a combination of one or more existing calibration models to predict the blood analytes.

7. An intelligent system for measuring blood analytes noninvasively by operating on a near infrared (NIR) absorbance spectrum of in vivo skin tissue, said system comprising:
- an execution layer that receives tissue absorbance spectra from an instrument and that performs rudimentary preprocessing;
- a coordination layer that performs feature extraction;
- a classification system that is used to classify a subject according to extracted features that represent the state and structure of a sample;
- wherein predictions from one or more existing calibration models are used to form an analyte estimate based on said classification.

8. The system of claim 7, further comprising:
- a management level for receiving said classification and blood analyte prediction, said management level taking action based on the certainty of said estimate, said management level coordinating all algorithmic events, monitoring performance based on class, adapting rules as necessary, and maintaining information regarding system state.

9. The system of claim 7, wherein said classification system uses classes that are mutually exclusive.

10. The system of claim 7, wherein said classification system applies fuzzy set theory to form a classifier and prediction rules which allow membership in more than one class.

11. The system of claim 7, wherein said instrument performs absorbance measurement through any of transmissive, diffuse reflectance, or alternate methods.

12. The system of claim 7, wherein said tissue absorbance spectrum is a vector $m = \Re^N$ of absorbance values pertaining to a set of N wavelengths $\lambda \in \Re^N$ that span the near infrared, and wherein number of necessary wavelengths in said spectrum is a function of cross correlation between a target analyte and interfering species.

13. The system of claim 7, further comprising:
- preprocessing means for scaling, normalization, smoothing, calculating derivatives, filtering, and other transformations that attenuate noise and instrumental variation without affecting the signal of interest.

14. The system of claim 13, wherein a preprocessed measurement, $x = \Re^N$ is determined according to:

$$x = h(\lambda, m)$$

where h: $\Re^{N \times 2} \to \Re^N$ is a preprocessing function.

15. The system of claim 7, wherein an entire spectrum is used for noninvasive applications with significant variation within and between individuals.

16. A pattern recognition method for estimating a concentration of a target blood analyte, comprising the step of:
- classifying new spectral measurements into previously defined classes through structural and state similarities as observed in a tissue absorbance spectrum, according to a pattern classification method;
- wherein class membership is an indication of which calibration model is most likely to accurately estimate the concentration of the target blood analyte;
- said pattern classification method comprising the steps of:
  - extracting features; and
  - classifying said features according to a classification model and decision rule.

17. The method of claim 16, wherein said feature extraction step is any mathematical transformation that enhances a particular aspect or quality of data that is useful for interpretation.

18. The method of claim 16, wherein said classification model comprises means for determining a set of similarity measures with predefined classes.

19. The method of claim 18, further comprising the step of:
- providing a classification system that assumes that said classes are mutually exclusive and that forces each measurement to be assigned to a single class.

20. The method of claim 18, further comprising the step of:
- providing a fuzzy classifier that is not mutually exclusive, wherein said fuzzy classifier allows a sample to have membership in more than one class simultaneously and provides a number between zero and one indicating a degree of membership in each class.

21. The method of claim 20, wherein a calibration model is passed a vector of memberships, where a vector, c, is used to determine an adaptation of said calibration model suitable for blood analyte prediction or an optimal combination of several blood analyte predictions.

22. The method of claim 21, wherein a membership vector and preprocessed absorbance spectrum are both used by a single calibration model for blood analyte prediction, where the calculation is given by:

$$\hat{y} = g(c, x)$$

where g(•) is a nonlinear mapping determined through any of nonlinear regression, nonlinear partial least squares, or artificial neural networks.

23. The method of claim 21, wherein separate calibrations are used for each class; and wherein each calibration is generated using all measurements in a calibration set by exploiting a membership vector assigned to each measurement.

24. The method of claim 23, wherein said membership vector is used to determine an optimal combination of p blood analyte predictions from all classes through defuzzification.

25. The method of claim 24, wherein each of the p calibration models is developed using an entire calibration.

26. The method of claim 25, wherein calibration measurements are weighted by their respective membership in a kth class when a kth calibration model is calculated; wherein weighted least squares is applied to calculate regression coefficients in a linear case, and wherein a covariance matrix is used in a factor based methods case.

27. The method of claim 24, wherein said defuzzification is a mapping from a vector of blood analyte predictions and a vector of class memberships to a single analyte prediction, wherein said defuzzifier can be denoted as transformation such that:

$$\hat{y} = d(c, [y_1\ y_2\ y_3\ \ldots\ y_p])$$

where $d(\bullet)$ is the defuzzification function, c is a class membership vector and $Y_k$ is a blood analyte prediction of a kth calibration model.

28. The method of claim 16, wherein said decision rule comprises means for assigning class membership on the basis of a set of measures calculated by a decision engine.

29. The method of claim 16, wherein said feature extraction step comprises any mathematical transformation that enhances a quality or aspect of sample measurement for interpretation to represent concisely structural properties and physiological state of a tissue measurement site, wherein a resulting set of features is used to classify a subject and determine a calibration model that is most useful for blood analyte prediction.

30. The method of claim 29, wherein said features are represented in a vector, $z \in \Re^M$ that is determined from a preprocessed measurement through:

$$z = f(\lambda, x)$$

where $f: \Re^N \to \Re^M$ is a mapping from a measurement space to a feature space, wherein decomposing $f(\bullet)$ yields specific transformations, $f_i(\bullet): \Re^N \to \Re^{M_i}$ for determining a specific feature, wherein the dimension, $M_i$, indicates whether an ith feature is a scalar or a vector and an aggregation of all features is the vector z, and wherein a feature exhibits a certain structure indicative of an underlying physical phenomenon when said feature is represented as a vector or a pattern.

31. The method of claim 30, wherein individual features are divided into two categories comprising:

abstract features that do not necessarily have a specific interpretation related to a physical system; and simple features that are derived from an a priori understanding of a sample and that can be related directly to a physical phenomenon.

32. The method of claim 31, wherein features that can be calculated from NIR spectral absorbance measurements include any of:

thickness of adipose tissue;
hematocrit level;
tissue hydration;
magnitude of protein absorbance;
scattering properties of said tissue;
skin thickness;
temperature related effects;
age related effects;
spectral characteristics related to sex;
pathlength estimates;
volume fraction of blood in tissue; and
spectral characteristics related to environmental influences.

33. The method of claim 16, further comprising the step of:

employing spectral decomposition to determine features related to a known spectral absorbance pattern.

34. The method of claim 16, further comprising the step of:

employing factor based methods to build a model capable of representing variation in a measured absorbance related to a demographic variable;

wherein projection of a measured absorbance spectrum onto said model constitutes a feature that represents spectral variation related to said demographic variable.

35. The method of claim 16, wherein said extraction step determines at least one calibration model that is most appropriate for measurement;

wherein a subject is assigned to one of many predefined classes for which a calibration model has been developed and tested.

36. The method of claim 16, wherein said pattern classification step further comprises the steps of:

measuring the similarity of a features to predefined classes; and assigning class membership.

37. The method of claim 36, wherein said measuring step uses mutually exclusive classes and assigns each measurement to one class.

38. The method of claim 36, wherein said assigning step uses a fuzzy classification system that allows class membership in more than one class simultaneously.

39. The method of claim 16, further comprising the step of:

assigning measurements in an exploratory data set to classes.

40. The method of claim 39, further comprising the step of:

using measurements and class assignments to determine a mapping from features to class assignments.

41. The method of claim 40, further comprising the steps of:

defining classes from said features in a supervised manner, wherein each set of features is divided into two or more regions, and wherein classes are defined by combinations of feature divisions;

designing a classifier subsequent to class definition through supervised pattern recognition by determining an optimal mapping or transformation from the feature space to a class estimate which minimizes the number of misclassifications; and creating a model based on class definitions which transforms a measured set of features to an estimated classification.

42. The method of claim 41, wherein a mapping from feature space to a vector of class memberships is given by:

$$c_k = f_k(z)$$

where k=1, 2, ... P, $f_k(\cdot)$ is membership function of the Kth class, $c_k \epsilon [0,1]$ for all K and the vector $c \epsilon \Re^P$ is the set of class memberships; wherein said membership vector provides a degree of membership in each of said predefined classes and is passes to a calibration algorithm, said calibration algorithm determining a combination of one or more calibration models for blood analyte prediction.

43. The method of claim 42, wherein blood analyte prediction occurs by application of said combination of one or more calibration models for blood analyte prediction.

44. The method of claim 43, wherein said calibration model comprises either of nonlinear partial least squares or artificial neural networks.

45. The method of claim 43, wherein a blood analyte prediction for a preprocessed measurement x with classification specified by c is given by:

$$\hat{y}=g(c,x)$$

where $g(\cdot)$ is a nonlinear calibration model which maps x and c to an estimate of the blood analyte concentration, $\bar{y}$.

46. The method of claim 43, wherein a different calibration is realized for each class.

47. The method of claim 46, wherein an estimated class is used to select one of p calibration models most appropriate for blood analyte prediction using a current measurement, wherein given that k is the class estimate for said measurement, blood analyte prediction is:

$$\hat{y}=g_k(x)$$

where $g_k(\cdot)$ is the calibration model associated with the kth class.

48. The method of claim 46, therein said calibrations are developed from a set of exemplar absorbance spectra with reference blood analyte values and pre-assigned classification definitions.

49. The method of claim 16, further comprising the step of:

providing an algorithm manager for reporting results to an operator, coordinating all algorithmic events, monitoring performance based on class, and adapting rules as necessary.

50. The method of claim 49, wherein both class estimates and blood analyte predictions are reported to said algorithm manager.

51. The method of claim 49, further comprising the step of:

notifying said operator by said algorithm manager that a prediction is invalid or a measurement does not fit into one of the existing classes; wherein further spectral measurements are taken to determine if said error is due to an instrument, a measurement technique, or a sample; and wherein said error detection and correction algorithm determines if more classes are necessary or if said instrument requires maintenance.

* * * * *